US010350439B2

(12) United States Patent
Maxwell et al.

(10) Patent No.: US 10,350,439 B2
(45) Date of Patent: Jul. 16, 2019

(54) FOCUSED ULTRASOUND APPARATUS AND METHODS OF USE

(71) Applicants: University of Washington through its Center for Commercialization, Seattle, WA (US); The Trustees of Columbia University in the City of New York, New York, NY (US)

(72) Inventors: Adam Maxwell, Seattle, WA (US); Ryan Hsi, Seattle, WA (US); Thomas Lendvay, Seattle, WA (US); Pasquale Casale, New York, NY (US); Michael Bailey, Seattle, WA (US)

(73) Assignees: University of Washington through its Center for Commercialization, Seattle, WA (US); The Trustees of Columbia University in the City of New York, New York, NY (US)

( * ) Notice: Subject to any disclaimer, the term of this patent is extended or adjusted under 35 U.S.C. 154(b) by 819 days.

(21) Appl. No.: 14/777,949

(22) PCT Filed: Mar. 28, 2014

(86) PCT No.: PCT/US2014/032219
§ 371 (c)(1),
(2) Date: Sep. 17, 2015

(87) PCT Pub. No.: WO2014/160964
PCT Pub. Date: Oct. 2, 2014

(65) Prior Publication Data
US 2016/0287909 A1    Oct. 6, 2016

Related U.S. Application Data
(60) Provisional application No. 61/806,295, filed on Mar. 28, 2013.

(51) Int. Cl.
*A61N 7/00* (2006.01)
*A61B 8/00* (2006.01)
(Continued)

(52) U.S. Cl.
CPC .............. *A61N 7/00* (2013.01); *A61B 8/0866* (2013.01); *A61B 8/44* (2013.01); *A61B 8/4444* (2013.01);
(Continued)

(58) Field of Classification Search
CPC ............ A61B 17/225; A61B 17/22004; A61B 17/320068; A61B 2017/00526; A61B 2560/0475
(Continued)

(56) References Cited

U.S. PATENT DOCUMENTS 8,057,408 B2    11/2011  Cain et al.
8,323,201 B2 *  12/2012  Towfiq ................. A61B 8/0825
                                                   600/437
(Continued)

FOREIGN PATENT DOCUMENTS

CN    2551208 Y    5/2003
CN    1669672 A    9/2005
(Continued)

OTHER PUBLICATIONS

Communication Pursuant to Article 94(3) EPC dated Jun. 7, 2017, issued in corresponding European Patent Application No. 14 723 604.6, filed Mar. 28, 2014, 8 pages.
(Continued)

*Primary Examiner* — Baisakhi Roy
(74) *Attorney, Agent, or Firm* — Christensen O'Connor Johnson Kindness PLLC

(57) ABSTRACT

Methods for diagnosing a pathologic tissue membrane, as well as a focused ultrasound apparatus and methods of
(Continued)

treatment are disclosed to perform ureterocele puncture noninvasively using focused ultrasound-generated cavitation or boiling bubbles to controllably erode a hole through the tissue. An example ultrasound apparatus may include (a) a therapy transducer having a treatment surface, wherein the therapy transducer comprises a plurality of electrically isolated sections, (b) at least one concave acoustic lens defining a therapy aperture in the treatment surface of the therapy transducer, (c) an imaging aperture defined by either the treatment surface of the therapy transducer or by the at least one concave acoustic lens and (d) an ultrasound imaging probe axially aligned with a central axis of the therapy aperture.

19 Claims, 17 Drawing Sheets

(51) Int. Cl.
    *A61B 8/08*     (2006.01)
    *A61N 7/02*     (2006.01)
    *A61B 90/00*     (2016.01)

(52) U.S. Cl.
    CPC ........ *A61N 7/02* (2013.01); *A61B 2090/3784* (2016.02); *A61N 2007/006* (2013.01); *A61N 2007/0065* (2013.01); *A61N 2007/0078* (2013.01); *A61N 2007/0086* (2013.01)

(58) Field of Classification Search
    USPC .......................................................... 601/2
    See application file for complete search history.

(56) References Cited

U.S. PATENT DOCUMENTS

| | | | |
|---|---|---|---|
| 2004/0059265 | A1 | 3/2004 | Candy et al. |
| 2009/0230822 | A1 | 9/2009 | Kushculey et al. |
| 2012/0016239 | A1 | 1/2012 | Barthe et al. |
| 2012/0215138 | A1* | 8/2012 | Zhong .............. A61B 17/22004 601/4 |
| 2012/0265227 | A1 | 10/2012 | Sverdlik et al. |
| 2013/0253387 | A1 | 9/2013 | Bonutti et al. |
| 2013/0289593 | A1* | 10/2013 | Hall ............... A61B 17/320068 606/169 |

FOREIGN PATENT DOCUMENTS

| | | |
|---|---|---|
| EP | 2 844 343 A1 | 3/2015 |
| JP | 6-319746 A | 11/1994 |
| JP | 2001-137256 A | 5/2001 |
| KR | 2013-0055972 A | 5/2013 |
| WO | 11/055316 A1 | 5/2011 |
| WO | 2011/055316 A1 | 5/2011 |
| WO | 12/156863 A2 | 11/2012 |
| WO | 2012/156863 A2 | 11/2012 |

OTHER PUBLICATIONS

Chinese Office Action dated Dec. 4, 2017, issued in Chinese Application No. 201480018473.2, filed Mar. 28, 2014, 8 pages.
Japanese Office Action dated Feb. 20, 2018, issued in Japanese Application No. 2016-505604, filed Mar. 28, 2014, 11 pages.
Aoki, H., et al., "Application of High-Intensity Focused Ultrasound for Fetal Therapy: Experimental Study Using an Animal Model of Lower Urinary Tract Obstruction," Journal of Medical Ultrasonics 40(2):107-110, Apr. 2013.
Byun, E., and P.A. Merguerian, "A Meta-Analysis of Surgical Practice Patterns in the Endoscopic Management of Ureteroceles," Journal of Urology 176(4 Pt. 2):1871-1877, Oct. 2006.
Campbell, M., "Ureterocele: A Study of 94 Instances in 80 Infants and Children," Surgery, Gynecology and Obstetrics 93(6):705-718, Dec. 1951.
Canney, M.S., et al., "Shock-Induced Heating and Millisecond Boiling in Gels and Tissue Due to High Intensity Focused Ultrasound," Ultrasound in Medicine and Biology 36(2):250-267, Feb. 2010.
Chertin, B., et al., "Is Primary Endoscopic Puncture of Ureterocele a Long-Term Effective Procedure?" Journal of Pediatric Surgery 38(1):116-119, Jan. 2003.
Di Benedetto, V., et al., "Transurethral Puncture of Ureterocele Associated With Single Collecting System in Neonates," Journal of Pediatric Surgery 32(9):1325-1327, Sep. 1997.
Griffin, J., et al., "Ultrasonic Evaluation of Simple and Ectopic Ureteroceles," Clinical Radiology 34(1):55-57, Jan.-Nov. 1983.
Hagg, M.J., et al., "The Modern Endoscopic Approach to Ureterocele," Journal of Urology 163(3):940-943, Mar. 2000.
Hall, T., and C. Cain, "A Low Cost Compact 512 Channel Therapeutic Ultrasound System for Transcutaneous Ultrasound Surgery," in G.T. Clement et al. (eds.), "Therapeutic Ultrasound: 5th International Symposium on Therapeutic Ultrasound," Boston, Oct. 27-29, 2005, AIP Conference Proceedings 829:445-449, May 2006.
Hall, T.L., et al., "Histotripsy of the Prostate: Dose Effects in a Chronic Canine Model," Urology 74(4):932-937, Oct. 2009.
Hall, T.L., et al., "A Real-Time Measure of Cavitation Induced Tissue Disruption by Ultrasound Imaging," IEEE Transactions on Ultrasonics, Ferroelectrics, and Frequency Control 54(3):569-575, Mar. 2007.
Han, M.Y., et al., "Indications for Nonoperative Management of Ureteroceles," Journal of Urology 174(4 Pt. 2):1652-1656, Oct. 2005.
Husmann, D., et al., "Management of Ectopic Ureterocele Associated With Renal Duplication: A Comparison of Partial Nephrectomy and Endoscopic Decompression," Journal of Urology 162(4):1406-1409, Oct. 1999.
Jesus, L.E., et al., "Clinical Evolution of Vesicoureteral Reflux Following Endoscopic Puncture in Children With Duplex System Ureteroceles," Journal of Urology 186(4):1455-1459, Oct. 2011.
Kajbafzadeh, A., et al., "Evolution of Endoscopic Management of Ectopic Ureterocele: A New Approach," Journal of Urology 177(3):1118-1123, Mar. 2007.
Khokhlova, T.D., et al., "Controlled Tissue Emulsification Produced by High Intensity Focused Ultrasound Shock Waves and Millisecond Boiling," Journal of the Acoustical Society of America 130(5):3498-3510, Nov. 2011.
Kim, Y., et al., "Developmental Impact and Lesion Maturation of Histotripsy-Mediated Non-Invasive Tissue Ablation in a Fetal Sheep Model," Ultrasound in Medicine and Biology 39(6):1047-1055, Jun. 2013.
Kreider, W., et al., "Holographic Reconstruction of Therapeutic Ultrasound Sources," Journal of the Acoustical Society of America 129(4):2403, Apr. 2011.
Lake, A.M. et al., "Histotripsy: Minimally Invasive Technology for Prostatic Tissue Ablation in an In Vivo Canine Model," Urology 72(3):682-686, Sep. 2008.
Maxwell, A.D., et al., "Noninvasive Treatment of Deep Venous Thrombosis Using Pulsed Ultrasound Cavitation Therapy (Histotripsy) in a Porcine Model," Journal of Vascular and Interventional Radiology 22(3):369-377, Mar. 2011.
Meir, D.B., et al., "Does the Endoscopic Technique of Ureterocele Incision Matter?" Journal of Urology 172(2):684-686, Aug. 2004.
Merguerian, P.A., et al., "Variation in Management of Duplex System Intravesical Ureteroceles: A Survey of Pediatric Urologists," Journal of Urology 184(4 Suppl.):1625-1630, Oct. 2010.
Palmer, B.W., et al., "Comparison of Endoscopic Ureterocele Decompression Techniques. Preliminary Experience—Is the Watering Can Puncture Superior?" Journal of Urology 186(4 Suppl.):1700-1704, Oct. 2011.
Parsons, J.E., et al., "Pulsed Cavitational Ultrasound Therapy for Controlled Tissue Homogenization," Utrasound in Medicine and Biology 32(1):115-129, Jan. 2006.
Pohl, H.G., et al., "Vesicoureteral Reflux and Ureteroceles," Journal of Urology 177(5):1659-1666, May 2007.

(56) References Cited

OTHER PUBLICATIONS

Quintero, R.A., et al., "In-Utero Treatment of Fetal Bladder Outlet Obstruction by a Ureterocele," Lancet 357(9272):1947-1948, Jun. 2001.

Rich, M.A., et al., "Low Transurethral Incision of Single System Intravesical Ureteroceles in Children," Journal of Urology 144(1):120-121, Jul. 1990.

Rickwood, A.M., et al., "Current Management of Duplex-System Ureteroceles: Experience With 41 Patients," British Journal of Urology 70(2):196-200, Aug. 1992.

Schade, G.R., et al., "Histotripsy Focal Ablation of Implanted Prostate Tumor in an ACE-1 Canine Cancer Model," Journal of Urology 188(5):1957-1964, Nov. 2012.

Shokeir, A.A., and R.J. Nijman, "Ureterocele: An Ongoing Challenge in Infancy and Childhood," BJU International 90(8):777-783, Nov. 2002.

Uson, A.C., et al., "Ureteroceles in Infants and Children: A Report Based on 44 Cases," Pediatrics 27(6):971-983, Jun. 1961.

Wilder, R.T., et al., "Early Exposure to Anesthesia and Learning Disabilities in a Population-Based Birth Cohort," Anesthesiology 110(4):796-804, Apr. 2009. (Author Manuscript provided, PMCID: PMC2729550, available in PMC Apr. 1, 2010, 19 pages).

Xu, Z., et al., "Controlled Ultrasound Tissue Erosion," IEEE Transactions on Ultrasonics, Ferroelectrics, and Frequency Control 51(6):726-736, Jun. 2004.

Xu, Z., et al., "Optical and Acoustic Monitoring of Bubble Cloud Dynamics at a Tissue-Fluid Interface in Ultrasound Tissue Erosion," Journal of the Acoustical Society of America 121(4):2421-2430, Apr. 2007.

Xu, Z., et al., "Size Measurement of Tissue Debris Particles Generated From Pulsed Ultrasound Cavitational Therapy—Histotripsy," Ultrasound in Medicine and Biology 35(2):245-255, Feb. 2009.

Yuldashev, P.V., and V.A. Khokhlova, "Simulation of Three-Dimensional Nonlinear Fields of Ultrasound Therapeutic Arrays," Acoustical Physics 57(3):334-343, May 2011.

\* cited by examiner

FOCUSED ULTRASOUND APPARATUS AND METHODS OF USE

CROSS-REFERENCE TO RELATED APPLICATIONS

This application is a US national phase of International Application No. PCT/US2014/032219 filed Mar. 28, 2014, which claims the benefit of the filing date of U.S. Provisional Patent Application Ser. No. 61/806,295, filed Mar. 28, 2013, which are hereby incorporated by reference in their entirety.

STATEMENT OF GOVERNMENT INTEREST

This invention was made with government support under 2T32DK007779-11A1 and 2R01EB007643-05, awarded by the National Institutes of Health (NIH). The United States government has certain rights in the invention.

BACKGROUND

Unless otherwise indicated herein, the materials described in this section are not prior art to the claims in this application and are not admitted to be prior art by inclusion in this section.

Ureteroceles are a thin cyst-like out-pouching of the ureter opening to the bladder beyond the ureterovesical junction, associated with febrile urinary tract infections, urinary retention, and renal obstruction or injury. Ureteroceles are often detected during fetal development and are treated after birth. Ureteroceles can be detected during prenatal or postnatal ultrasonography, either incidentally or during investigation of related symptoms such as hydronephrosis. The diagnosis of ureteroceles most commonly occurs in the pediatric population, after workup of a urinary tract infection ("UTI"), bladder outlet obstruction, or abdominal pain. Treatment varies with ureterocele form and severity of symptoms. Current methods to treat ureteroceles include open surgical reconstruction, endoscopic puncture of the ureterocele wall, and observation. Endoscopic puncture is favored over open surgical reconstruction if treatment is needed due to its minimally-invasive approach. Specifically, endoscopic puncture involves inserting an instrument through the urethra to the bladder and utilizes an electrode or laser to create one or more small incisions to decompress the ureteroceles and relieve obstruction of urinary flow. While this technique is less invasive than open repair, instrumentation may seed bacteria into the urine and lead to a UTI. Furthermore, there are concerns regarding the use of general anesthesia in children, especially neonates. In addition, this procedure is typically done after birth at which point kidney damage, caused by chronic urinary obstruction, may already be evident. Individual cases of treatment in utero have been reported, but are uncommon.

SUMMARY

Example embodiments provide a focused ultrasound apparatus and methods of use to perform ureterocele puncture noninvasively using focused ultrasound-generated cavitation or boiling bubbles to controllably erode a hole through the tissue. The ultrasound energy may be focused and delivered transcutaneously to the target to cause localized tissue breakdown into subcellular fragments. As such, the resulting hole is not just an incision or tear in the wall of the ureteroceles, but is the result of removal of a substantially circular section of the tissue. This has the advantage of reducing incidence of a future re-obstruction. The finely focused energy of the invention through the skin of the patient may beneficially cause a perforation in tissue without degrading surrounding tissue. In one embodiment, ultrasound imaging may provide feedback to an operator for precise position for treatment and detection of the puncture. The noninvasive approach provided by the invention may potentially be performed in utero or after birth to treat ureteroceles minimizing the risks of anesthesia and infections. The focused ultrasound apparatus and methods may also be beneficially used to treat newborn babies with congenital heart abnormalities, posterior urethral valves or obstructive uropathy or to treat any patient with a cardiac abnormality, ovarian or renal cysts, cysts in other organs or soft tissues, valves in veins requiring puncturing (i.e., vein stripping), polycystic kidney disease, a posterior urethral valve, obstructive uropathy, acquired or congenital cystic kidney disease, calyceal diverticulum, acquired or congenital urethral stricture disease or ureteral stricture disease, congenital cystic adenomatoid malformation or other cystic lesions in a lung, need for a shunt in the brain or need for a bypass of cerebrospinal fluid or blood in the brain, a blockage in a Eustachian tube of the ear, congenital malformations of the esophagus, trachea, bowel or stomach such as pyloric stenosis, obstructed sinuses in the face or congenital or acquired obstruction of the uterus or vagina, or any other thin membrane tissue structure requiring puncturing.

Thus, in one aspect, an ultrasound apparatus is provided having (a) a therapy transducer having a treatment surface, wherein the therapy transducer comprises a plurality of electrically isolated sections, (b) at least one concave acoustic lens defining a therapy aperture in the treatment surface of the therapy transducer, (c) an imaging aperture defined by either the treatment surface of the therapy transducer or by the at least one concave acoustic lens and (d) an ultrasound imaging probe axially aligned with a central axis of the therapy aperture.

In another aspect, a method for treating a pathologic tissue membrane is provided including the steps of (a) placing a coupling head of an ultrasound apparatus in contact with a subject's skin, where the subject or a subject's in utero fetus has a pathologic tissue membrane in need of puncturing, where the ultrasound apparatus comprises a therapy transducer having a treatment surface, (b) obtaining image feedback of the tissue via the ultrasound imaging probe, (c) aligning a focal point of the therapy transducer with the tissue based upon at least the image feedback, (d) directing an effective amount of focused ultrasound at the tissue via the therapy transducer and (e) puncturing a hole in the tissue via the focused ultrasound.

In a further aspect, a method for diagnosing a pathologic tissue membrane is provided including the steps of (a) placing a coupling head of an ultrasound apparatus in contact with a subject's skin, wherein the ultrasound apparatus comprises (i) a therapy transducer having a treatment surface, wherein the therapy transducer comprises a plurality of electrically isolated sections, (ii) at least one concave acoustic lens defining a therapy aperture in the treatment surface of the therapy transducer, (iii) an imaging aperture defined by either the treatment surface of the therapy transducer or by the at least one concave acoustic lens and (iv) an ultrasound imaging probe axially aligned with a central axis of the therapy aperture, (b) obtaining image feedback of a tissue via the ultrasound imaging probe, and (c) determining whether the subject or a subject's in utero fetus has a pathologic tissue membrane in need of puncturing.

These as well as other aspects, advantages, and alternatives, will become apparent to those of ordinary skill in the art by reading the following detailed description, with reference where appropriate to the accompanying drawings.

DETAILED DESCRIPTION

Figure 1:
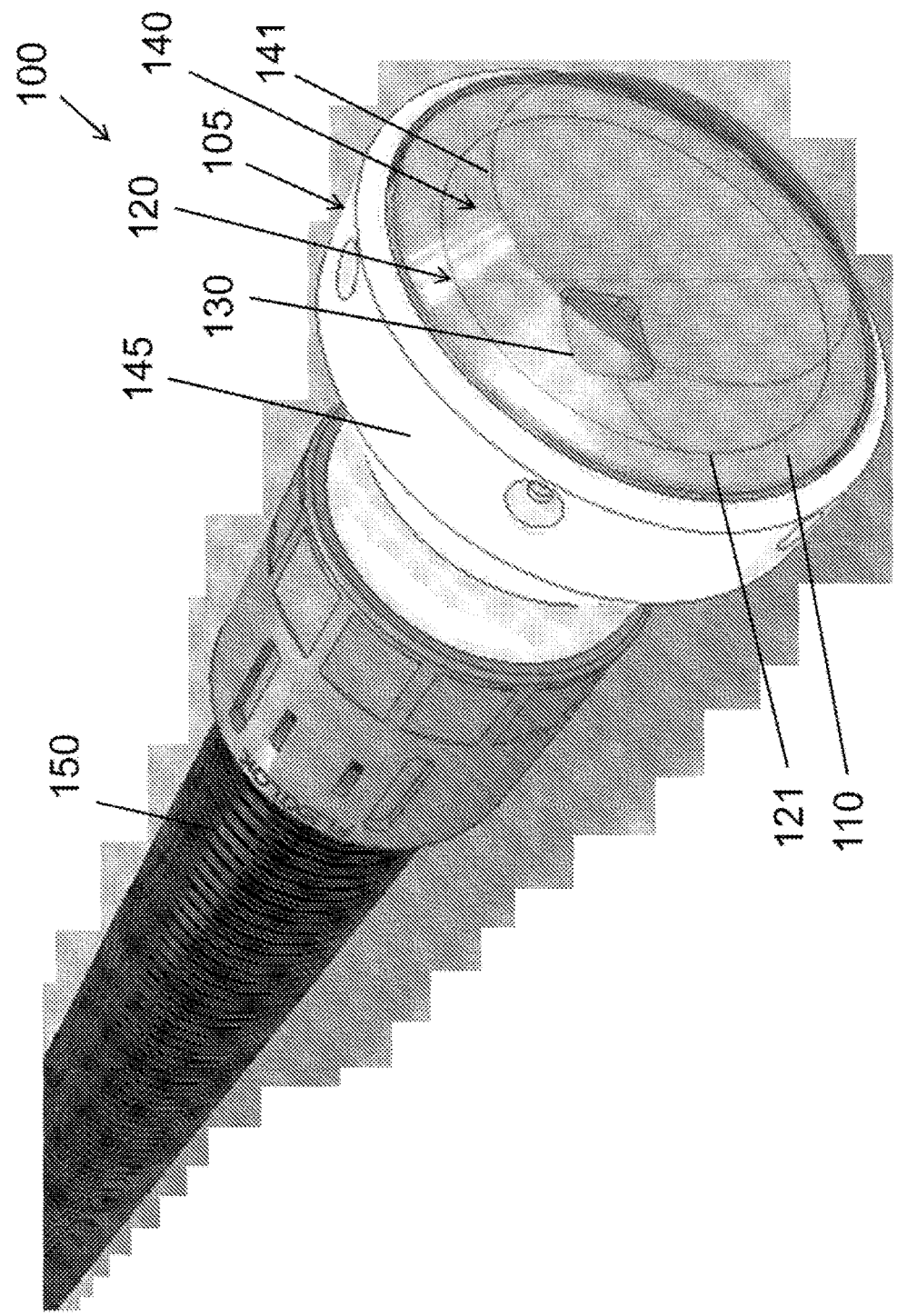
FIG. 1 is perspective view of the ultrasound apparatus according to an example embodiment.

Example ultrasound apparatus, methods of treatment and methods of diagnosing are described herein. Any example embodiment or feature described herein is not necessarily to be construed as preferred or advantageous over other embodiments or features. The example embodiments described herein are not meant to be limiting. It will be readily understood that certain aspects of the disclosed apparatus and methods can be arranged and combined in a wide variety of different configurations, all of which are contemplated herein.

Furthermore, the particular arrangements shown in the Figures should not be viewed as limiting. It should be understood that other embodiments may include more or less of each element shown in a given Figure. Further, some of the illustrated elements may be combined or omitted. Yet further, an example embodiment may include elements that are not illustrated in the Figures.

As used herein. "about" means+/−5%.

As used herein, a "tissue membrane" means a thin layer of cells, cellular tissue or connective tissue that covers, separates, and/or lines a tissue or organ, or that contains fluid within an organ. The tissue membrane can be one that covers, separates, or lines any tissue or organ, including but not limited to ureter, urethra, cardiac tissue, bladder, prostate, cyst, kidney, liver, nerve, artery, sail, sheath, penis, uterus, vagina, lung, brain, tympanic membrane, valve, and vein.

As used herein, "puncturing" means mechanical erosion of a tissue membrane or localized tissue breakdown into subcellular fragments. The puncture may take the form of a single hole, a series of smaller spaced apart holes or a linear incision. The size and shape of the punctured hole or incision can be varied based upon the width of the ultrasound at the focal point or high pressure zone.

The present embodiments advantageously provide methods for diagnosing a pathologic tissue membrane, as well as a focused ultrasound apparatus and methods of treatment to perform tissue membrane puncture noninvasively using focused ultrasound-generated cavitation or boiling bubbles to controllably erode a hole through the tissue. In one aspect, the invention provides an ultrasound apparatus, comprising:

a therapy transducer having a treatment surface, wherein the therapy transducer comprises a plurality of electrically isolated sections;

at least one concave acoustic lens defining a therapy aperture in the treatment surface of the therapy transducer;

an imaging aperture defined by either the treatment surface of the therapy transducer or by the at least one concave acoustic lens; and an ultrasound imaging probe axially aligned with a central axis of the therapy aperture.

Referring now to FIGS. 1-7, an ultrasound apparatus 100 is shown including a therapy transducer 105 having a treatment surface 110. The therapy transducer 105 may include a plurality of electrically isolated sections 115. The electrically isolated sections 115 of the therapy transducer 105 are configured to generate ultrasound radiation in response to the application of electric current thereto. For example, in one embodiment, the electrically isolated sections may be a piezoelectric ceramic material, and the electric current may be supplied via wires 116 connected to the front and back surfaces of each electrically isolated section 115, as shown in FIGS. 6C-6F. In various other embodiments, the active transducer material used for the electrically isolated sections 115 may include piezoelectric ceramics, piezoelectric ceramic-composites and/or crystals, among other possibilities.

The ultrasound apparatus 100 may also include at least one concave acoustic lens 120 defining a therapy aperture 121 in the treatment surface 110 of the therapy transducer 105. In one embodiment, shown in FIGS. 1-6H, a single concave acoustic lens 120 may be provided. The single acoustic lens 120 is preferably sized to be coextensive with the treatment surface 110 of the therapy transducer 105. This arrangement beneficially utilizes the entire active area of the electrically isolated sections 115 of the therapy transducer 105 and is therefore very efficient. This arrangement also advantageously allows the ultrasound apparatus 100 to maintain a smaller therapeutic window with an ultrasound focal point 125 that may aid in treating an utero fetus or infant. In this embodiment, the single acoustic lens 120 may include a plurality of sectors 122 and each sector 122 may have a radius of curvature. For example, the curvature of each sector 122 of the acoustic lens 120 may be defined by a concave elliptical profile such that the major axis is aligned in the direction towards the focal point 125 of the transducer 105. The length of each of the major and minor axes of the elliptical profile may be calculated to focus ultrasound generated by the given electrically-isolated section 115 to the focal point 125 of the transducer 105. The radius of curvature of the sectors 122 of the acoustic lens 120 may aid in focusing of the ultrasound generated by the electrically isolated sections 115 of the therapy transducer 105. In one embodiment, the radius of curvature of each of the plurality of sectors 122 of the acoustic lens 120 may be smaller than a radius of curvature of the acoustic lens 120 itself. In a further embodiment, the radius of curvature of each of the plurality of sectors 122 of the acoustic lens 120 may be the same. In operation, the radius of curvature of each sector 122 of the acoustic lens 120 may direct the ultrasound and focus the ultrasound on the focal point 125.

In one embodiment, each of the plurality of electrically isolated sections 115 of the therapy transducer 105 may be coupled to one of the plurality of sectors 122 of the single acoustic lens 120, such that there is a 1:1 ratio of electrically isolated sections 115 to sectors 122 of the acoustic lens 120. The electrically isolated sections 115 may be coupled to the sectors 122 of the acoustic lens 120 via an adhesive 126, for example, among other possibilities. In one embodiment, each electrically isolated section 115 of the therapy transducer 105 may be a flat piezoelectric ceramic material that is shaped to substantially match the footprint of each sector 122 of the acoustic lens 120. In various embodiments, the plurality of sectors 122 of the acoustic lens 120 may be between 4 sectors to 100 sectors. In various other embodiments, each electrically isolated section 115 may be further divided into multiple electrically isolated sub-sections such that each section 115 maintains the same footprint relative to a given sector of the acoustic lens 120. In this form, the electrically isolated sections 115 may comprise a phased array that provides further control to an operator to adjust the focal point 125. As the number of sectors 122 of the acoustic lens 120 increases, the ability to make the focal point 125 more symmetric also increases. A preferred embodiment has an acoustic lens 120 with ten to twelve sectors 122, this arrangement permits efficient distribution of power to each electrically isolated section 115, while at the same time providing the necessary amplitude of ultrasound to each electrically isolated section 115. In one embodiment, each of the plurality of sectors 122 of the acoustic lens 120 is configured to direct ultrasound to a focal point 125. For example, in operation, the ultrasound generated in the electrically isolated sections 115 may travel through the adhesive layer 126, through the acoustic lens 120 and out of the therapy transducer 105 to the focal point 125. In one embodiment, the focal point 125 may lie on the central axis 127 of the therapy aperture 121, and the focal point 125 may range from about 1 cm to about 18 cm from a center of the therapy aperture 121.

Figure 7:
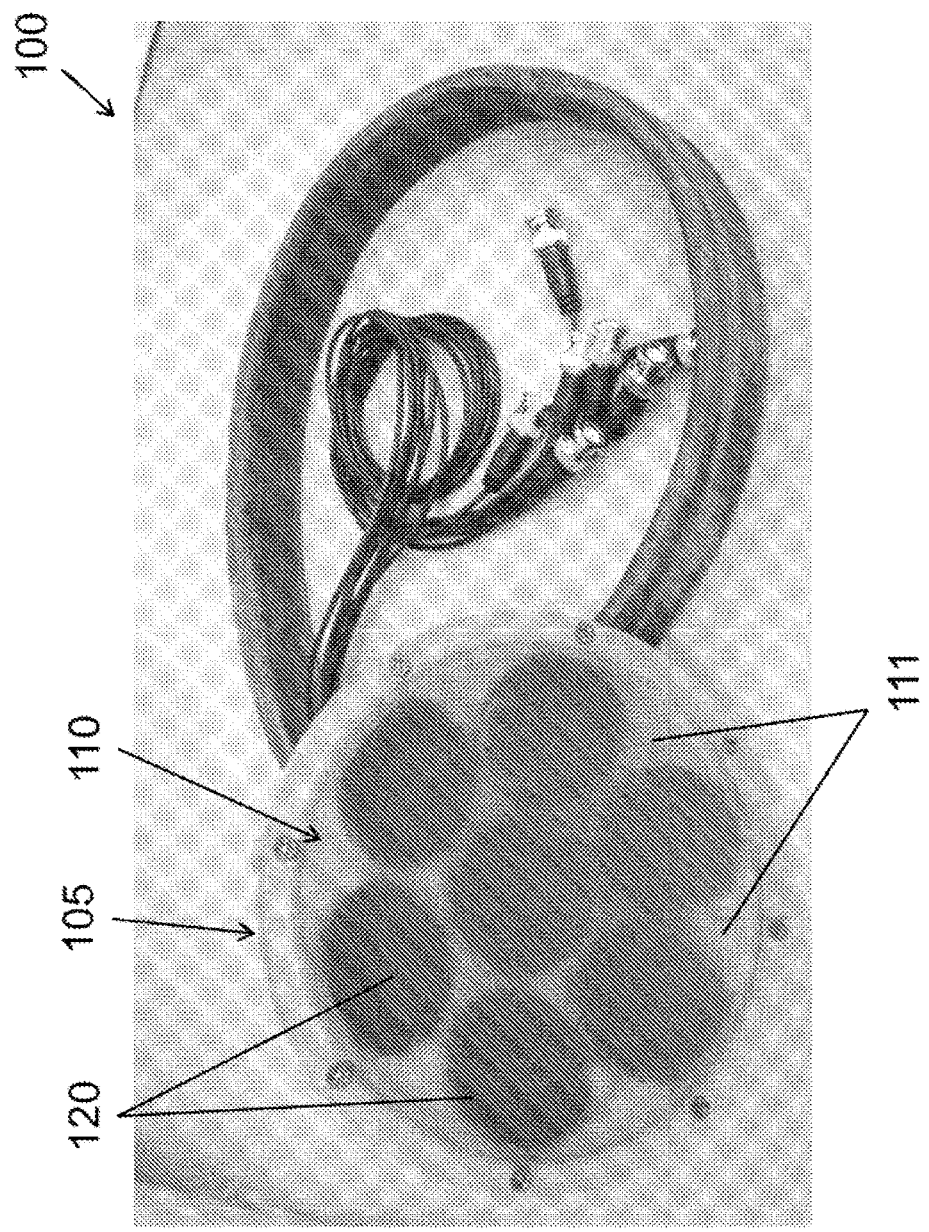
FIG. 7 is a front perspective view of the ultrasound apparatus having a plurality of concave acoustic lenses, according to one example embodiment.

In another embodiment, as shown in FIG. 7, the ultrasound apparatus 100 may be a plurality of concave acoustic lenses 122 and each of the plurality of electrically isolated sections 115 of the therapy transducer 105 may be coupled to one of the plurality of acoustic lenses 122. In one embodiment, the plurality of concave acoustic lenses 122 may be between 4 acoustic lenses to 100 acoustic lenses. This arrangement may not be as efficient as the arrangement in which a single acoustic lens 122 is substantially coextensive with the treatment surface 110 of the therapy transducer 105, since portions 111 of the treatment surface 110 are not being harnessed to direct ultrasound at the focal point 125. In one embodiment, each electrically isolated section 115 of the therapy transducer 105 may be a circular flat piezoelectric ceramic material that is shaped to substantially match the footprint of each concave acoustic lens 120.

In still another embodiment, the plurality of electrically isolated sections 115 of the therapy transducer 105 may each have a radius of curvature and together define a single acoustic lens 120. In other words, the ceramic piezoelectric material may be curved instead of flat and thereby define the acoustic lens 120. In one embodiment, the radius of curvature of each of the plurality of electrically isolated sections 115 of the therapy transducer 105 may be smaller than a radius of curvature of the single acoustic lens 120. In one embodiment, the plurality of electrically isolated sections 115 of the therapy transducer 105 may be between 4 sections and 100 sections. In various other embodiments, each electrically isolated section 115 may be further divided into multiple electrically isolated sub-sections. In this form, the electrically isolated sections 115 may comprise a phased array that provides further control to an operator to adjust the focal point 125.

The ultrasound apparatus 100 may also include an imaging aperture 130 defined by either the treatment surface 110 of the therapy transducer 105 or by a concave acoustic lens 120 that shares a central axis 127 with the therapy aperture 121. In a preferred embodiment, the imaging aperture 130 may be aligned with the central axis 127 of the therapy aperture 121. The ultrasound apparatus 100 may further include an ultrasound imaging probe 135 axially aligned with the central axis 127 of the therapy aperture 121 and the imaging probe 135. In various embodiments, the imaging probe may be configured for B-mode ultrasound or Doppler ultrasound imaging, including color Doppler. In operation, the imaging probe 135 may permit diagnosis of a tissue structural defect. The imaging probe 135 may further permit alignment of the therapy aperture 121 and ultrasound focal point 125 with the tissue structural defect, monitoring of the directed focused ultrasound during treatment and detection of cavitation bubbles from the directed focused ultrasound in a flow channel through a hole eroded through the tissue structural defect.

In one embodiment, the ultrasound apparatus 100 may further include a coupling head 140 coupled to and extending from the treatment surface 110 of the therapy transducer 105. In one embodiment, shown in FIGS. 1-3, the coupling head 140 may be angled inward toward the central axis 127 of the therapy aperture 121. In one embodiment, the coupling head 140 may circumscribe the single acoustic lens 120 (FIGS. 1-3) or the plurality of acoustic lenses 120 (FIG. 7). In one embodiment, the coupling head 140 may include a membrane 141, and a fluid may be enclosed between the acoustic lens 120, or plurality of lenses 120, and the membrane 141 of the coupling head 140. In an alternative embodiment, the coupling head 140 may be a solid planar disc. In one embodiment, the thickness of the planar disc may be less than or equal to about 5 cm. In one embodiment, the coupling head may be flexible. In various embodiments, the coupling head 140 may be made of flexible materials such as rubber, hydrogels, or other solid gels, among other possibilities. In use, ultrasound may be generated by the electrically isolated sections 115 of the therapy transducer 105 and travel through the sectors 122 of the acoustic lens 120, where the ultrasound becomes focused, and travel through the coupling head 140 and through the skin of the subject to the tissue defect.

Figure 2:
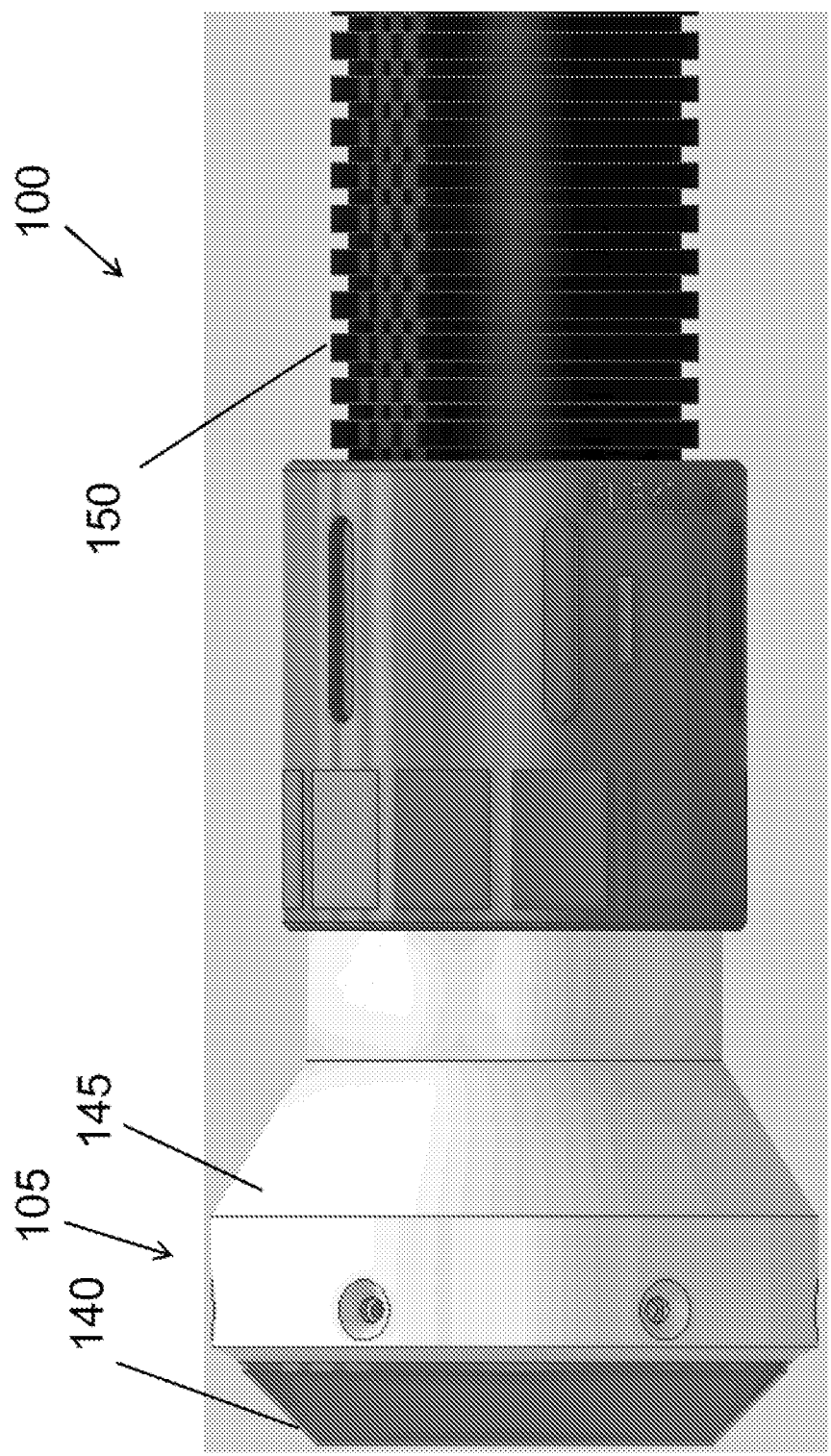
FIG. 2 is a side view of the ultrasound apparatus according to the example embodiment of FIG. 1.
Figure 3:
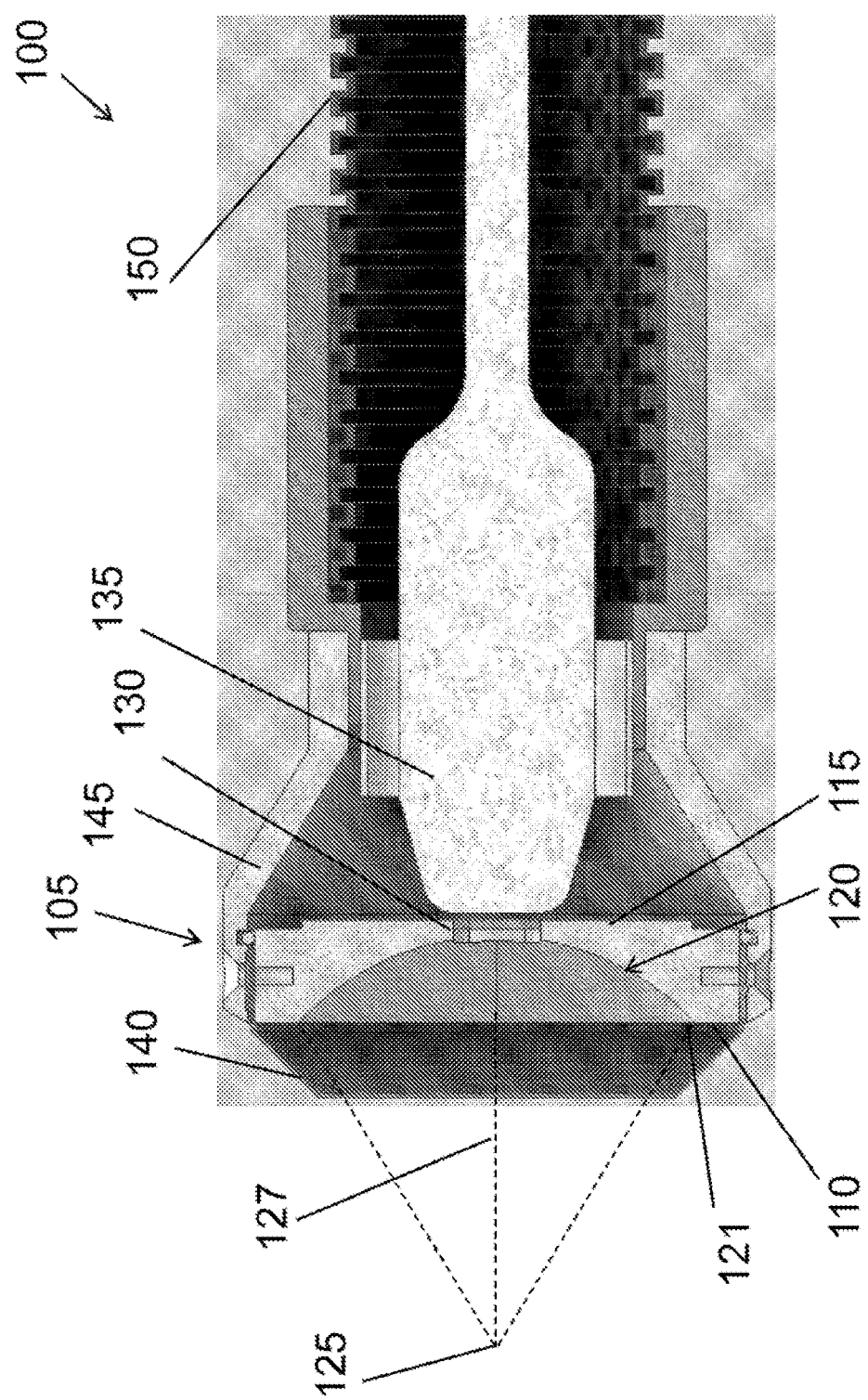
FIG. 3 is a cross-sectional side view of the ultrasound apparatus according to the example embodiment of FIG. 1.
Figure 4:
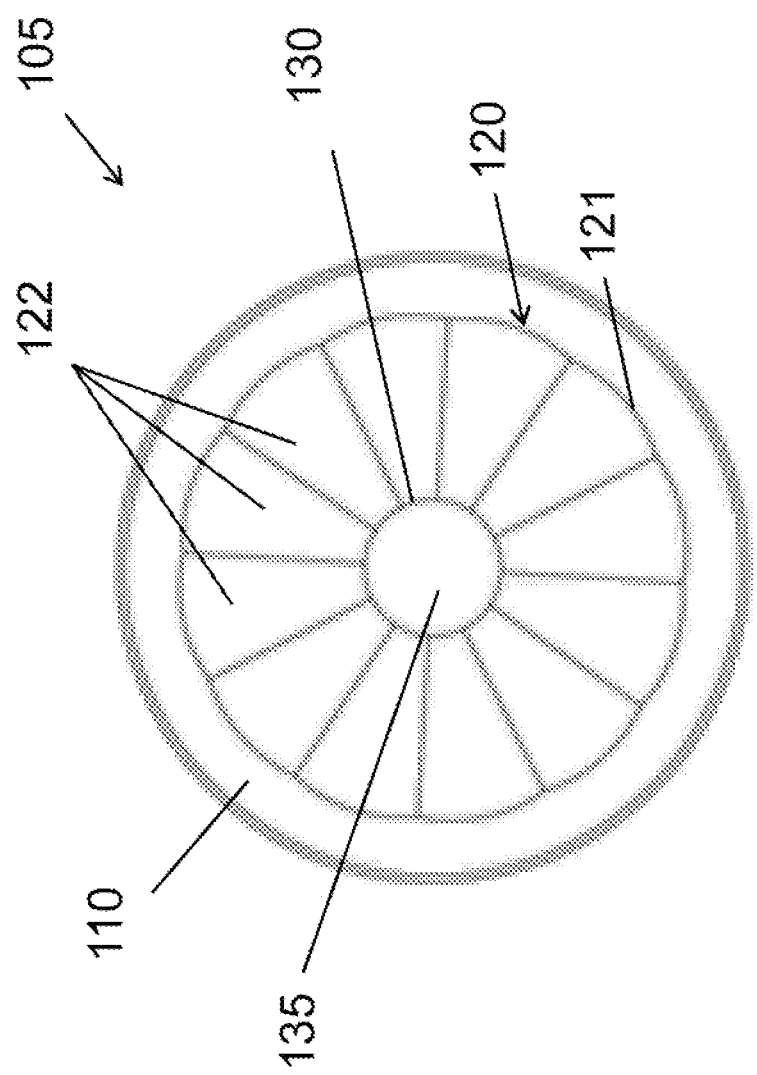
FIG. 4 is a front view of the ultrasound apparatus according to the example embodiment of FIG. 1.
Figure 5:
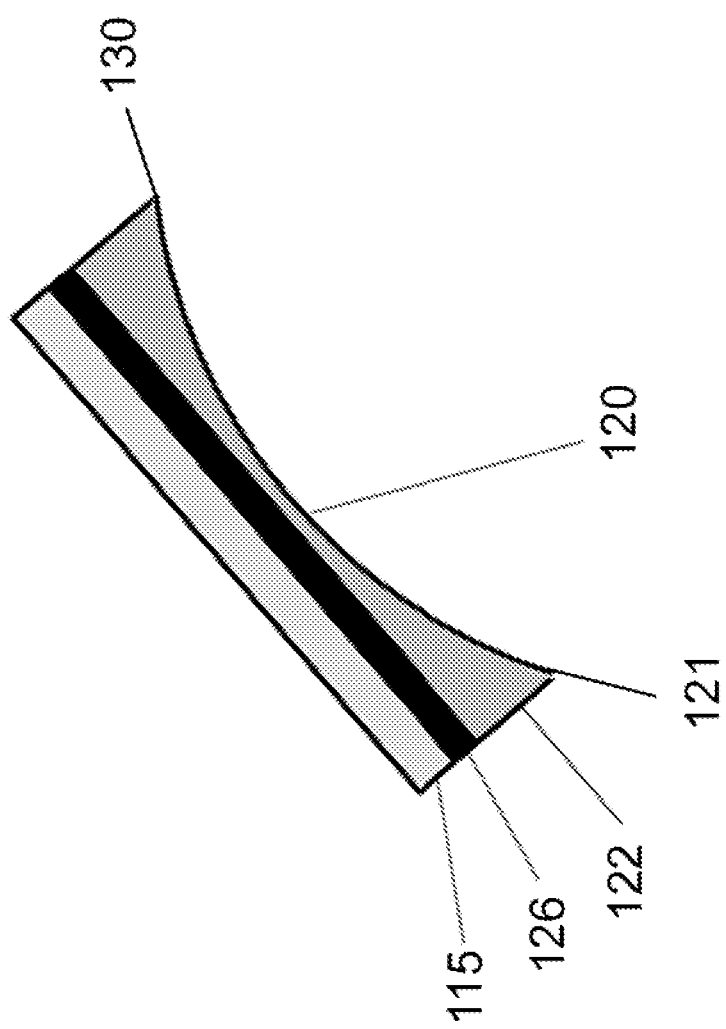
FIG. 5 is a side cross-sectional view of an electrically isolated section of a therapy transducer coupled to a sector of an acoustic lens that has a radius of curvature, according to one example embodiment.
Figure 6B:
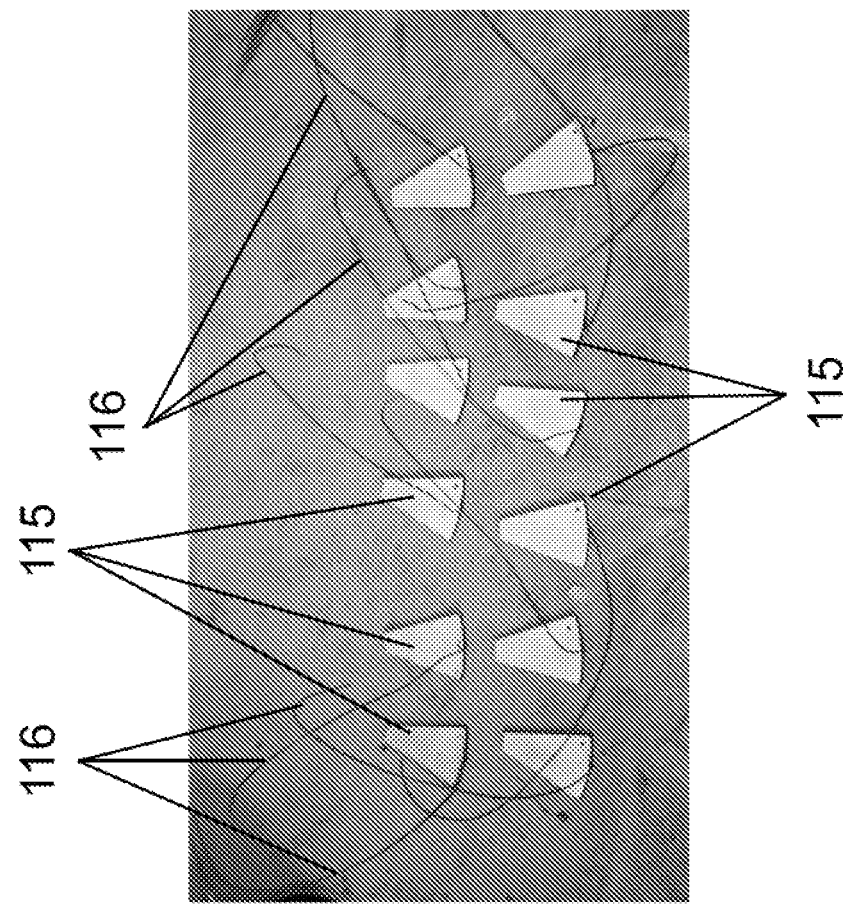
FIG. 6B is a back perspective view of a plurality of electrically isolated sections of a therapy transducer each having a wire coupled to the front face, according to one example embodiment.
Figure 6A:
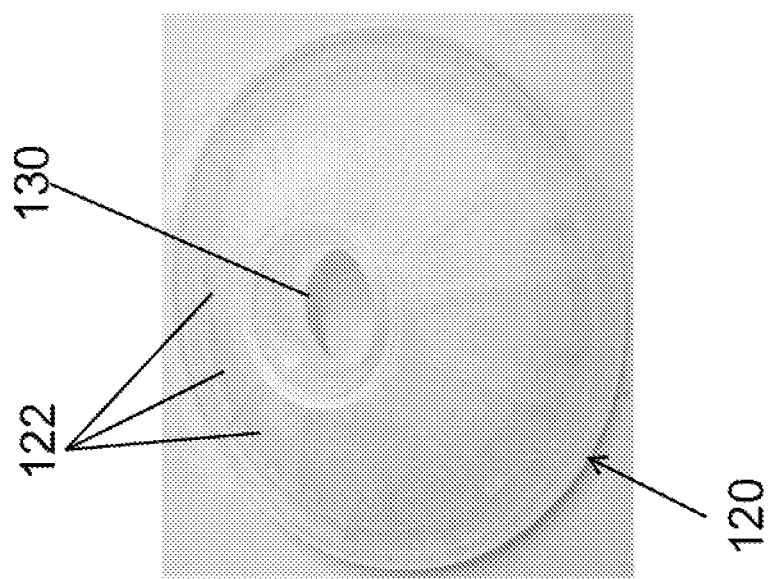
FIG. 6A is a back perspective view of a single concave acoustic lens, according to one example embodiment.
Figure 6D:
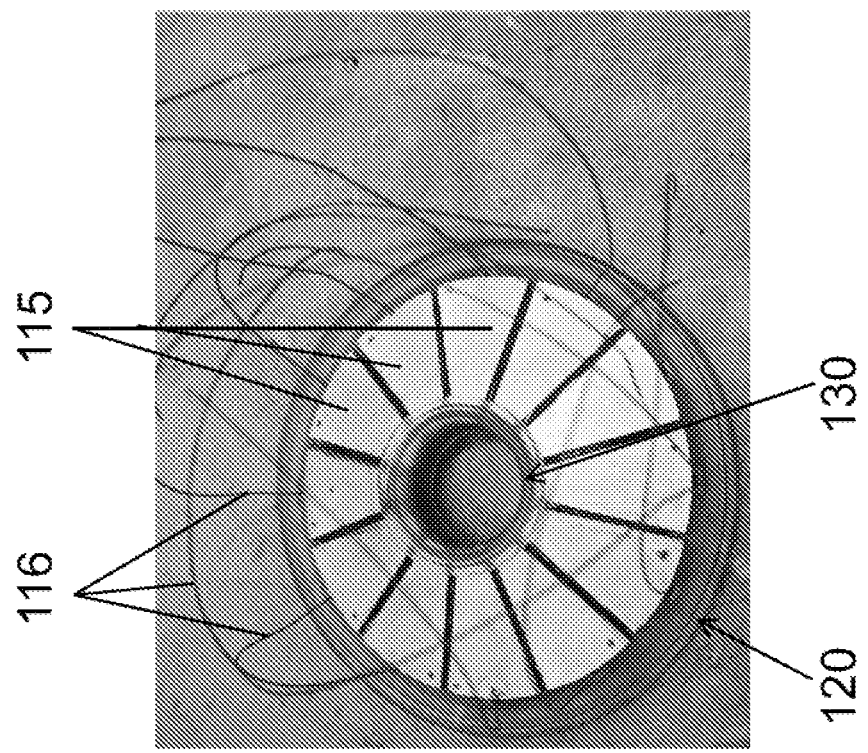
FIG. 6D is a back perspective view of the plurality of electrically isolated sections of a therapy transducer (shown in FIG. 6A) coupled to the entire back surface of the single concave acoustic lens (shown in FIG. 6B) via a bonding agent, according to one example embodiment.
Figure 6C:
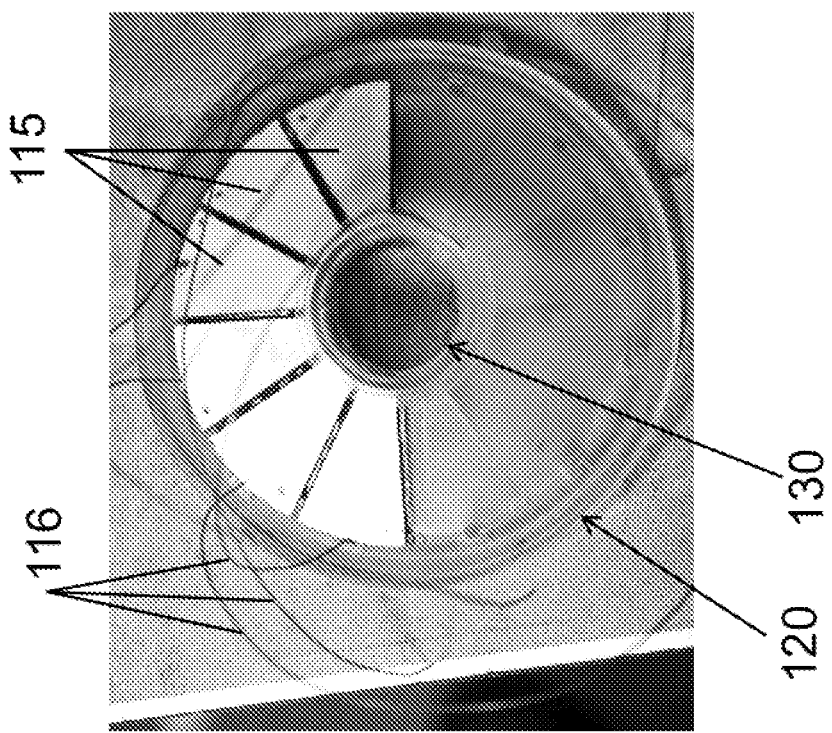
FIG. 6C is a back perspective view of the plurality of electrically isolated sections of a therapy transducer (shown in FIG. 6A) coupled to the top half of the back surface of the single concave acoustic lens (shown in FIG. 6B) via a bonding agent, according to one example embodiment.
Figure 6F:
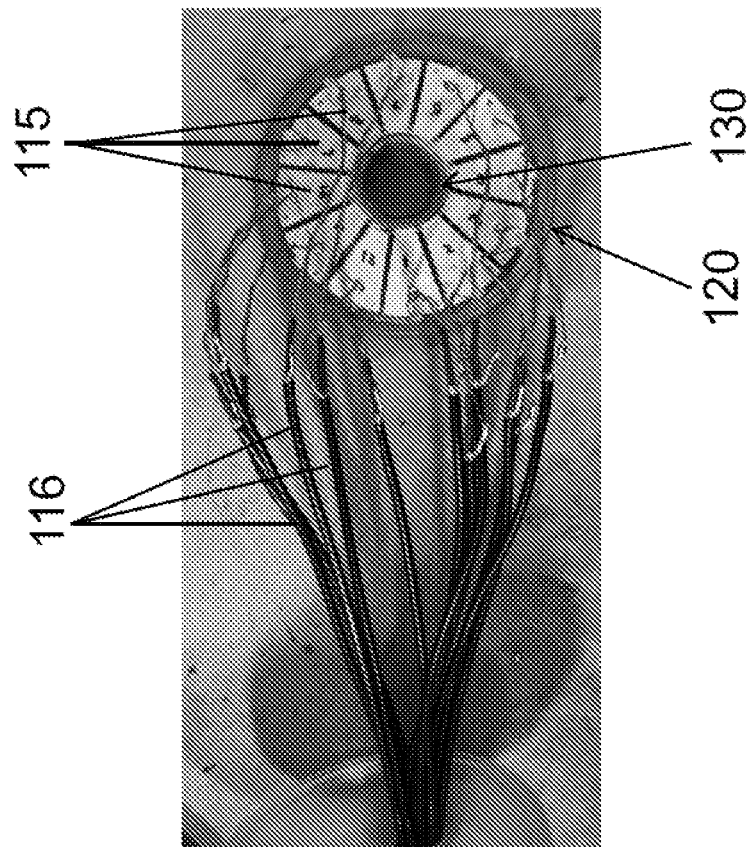
FIG. 6F is a back perspective view of the plurality of electrically isolated sections of a therapy transducer coupled to the entire back surface of the single concave acoustic lens via a bonding agent, where the wires attached to the front and back side of each electrically isolated section of the therapy transducer are separately bundled for connection to an amplifier and/or a control system, according to one example embodiment.
Figure 6E:
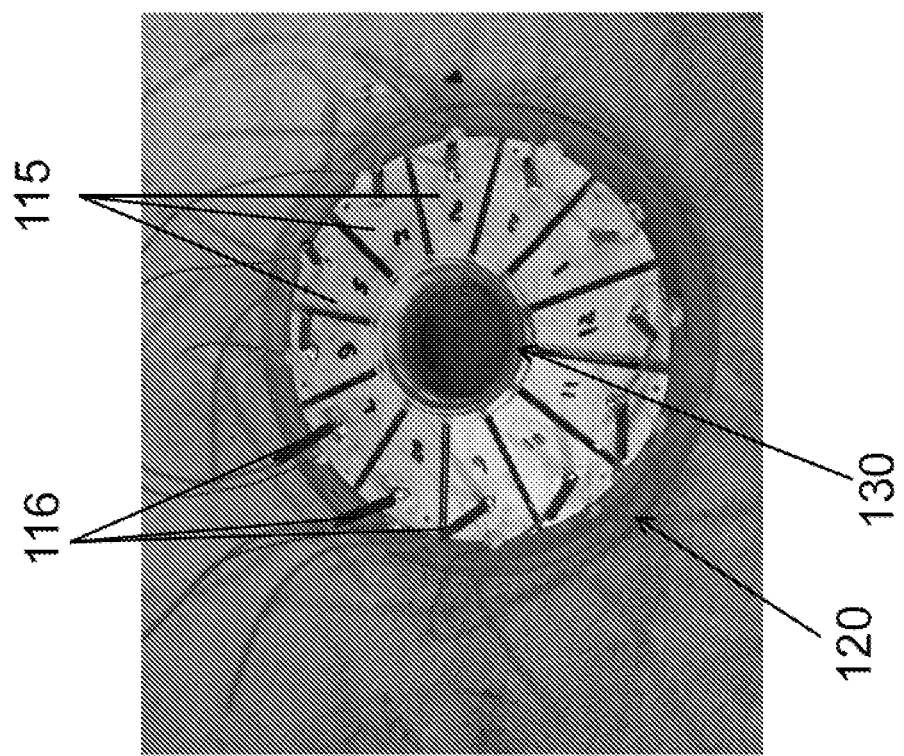
FIG. 6E is a back perspective view of the plurality of electrically isolated sections of a therapy transducer coupled to the entire back surface of the single concave acoustic lens via a bonding agent, where a wire is attached to the back side of each electrically isolated section of the therapy transducer, according to one example embodiment.
Figure 6H:
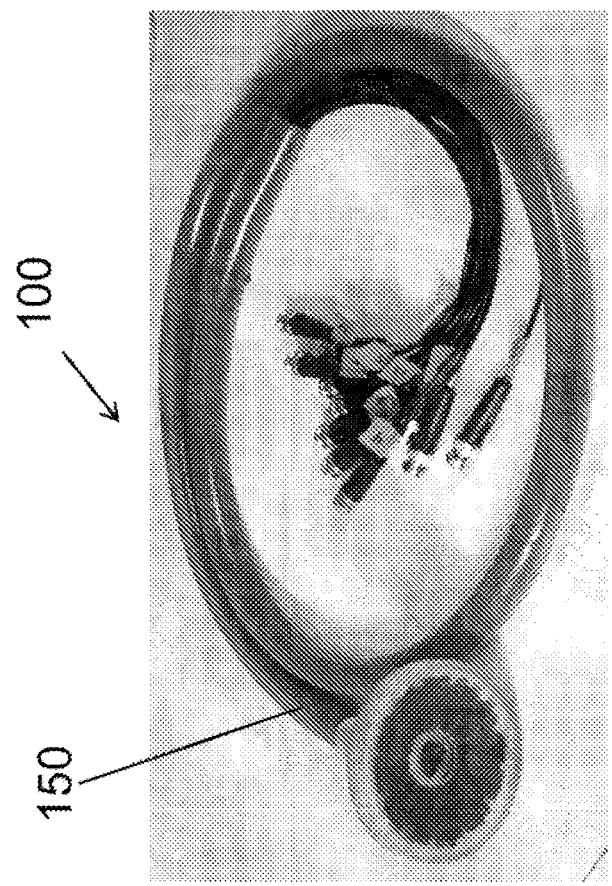
FIG. 6H is a front perspective view of the ultrasound device according to the example embodiment of FIGS. 6A-6G.
Figure 6G:
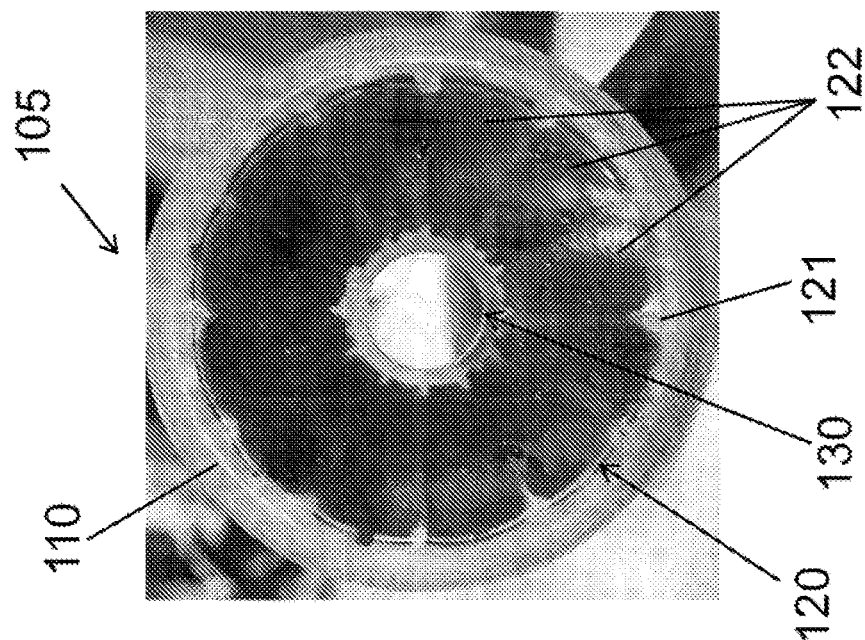
FIG. 6G is a front view of the plurality of electrically isolated sections of a therapy transducer (shown in FIG. 6A) coupled to the entire back surface of the single concave acoustic lens (shown in FIG. 6B) via a bonding agent, according to the example embodiment of FIG. 6D.

In one embodiment, as shown in FIGS. 1-3, the ultrasound apparatus 100 may include a housing 145 that at least partially surrounds the plurality of electrically isolated sections 115 of the therapy transducer 105 and the imaging probe 135. In another embodiment, the electrical coupling or wires 116 extending from the electrically isolated sections 115 of the transducer 105 may be disposed within a flexible cable conduit 150.

In another embodiment, the ultrasound apparatus 100 may include an amplifier electrically coupled to the therapy transducer 105. In a further embodiment, the ultrasound apparatus 100 may include a control system configured to control the amplifier and alter parameters associated with the focused ultrasound as described below with respect to the methods for treating a pathologic tissue membrane.

In a further embodiment, the ultrasound apparatus 100 may be sized and shaped to be hand-held. In another embodiment, the ultrasound apparatus 100 may be coupled to an articulating arm that may be manually manipulated by an operator or moved into position automatically via a control system to hold the ultrasound apparatus 100 in place during administration of the focused ultrasound. In yet another embodiment, a plurality of ultrasound devices 100 may be coupled to a belt to achieve multiple tissue punctures from different ultrasound focal points.

In another aspect, the invention provides methods for treating a pathologic tissue membrane, comprising:

placing a coupling head of an ultrasound apparatus in contact with a subject's skin, wherein the subject or a subject's in utero fetus has a pathologic tissue membrane in need of puncturing, wherein the ultrasound apparatus comprises a therapy transducer having a treatment surface;

obtaining image feedback of the tissue via the ultrasound imaging probe:

aligning a focal point of the therapy transducer with the tissue based upon at least the image feedback:

directing an effective amount of focused ultrasound at the tissue via the therapy transducer; and puncturing at least one hole or at least one linear incision in the tissue via the focused ultrasound.

As disclosed herein, the inventors have discovered that the methods of this aspect of the invention can be used, for example, noninvasively to perform tissue membrane puncture to a subject in need thereof using focused ultrasound-generated cavitation or boiling bubbles to controllably erode a hole through the tissue. The ultrasound energy may be focused and delivered transcutaneously to the target to cause localized tissue breakdown into subcellular fragments. As such, the resulting hole is not just an incision or tear in the wall of the tissue membrane, but is the result of removal of a substantially circular section of the tissue. This has the advantage of reducing incidence of a future re-obstruction. The finely focused energy of the invention through the skin of the patient may beneficially cause a perforation in tissue without degrading surrounding tissue.

The methods of the invention can be used to treat any suitable subject, such as a human subject with a pathologic tissue membrane that can benefit from controllably eroding a hole through the tissue with the defect. In various non-limiting embodiments, the pathologic tissue membrane may be in a tissue, including but not limited to ureter, urethra, cardiac tissue, bladder, prostate, cyst, kidney, liver, nerve, artery, sail, sheath, penis, uterus, vagina, lung, brain, tympanic membrane, esophagus, trachea, bowel, stomach, sinus, valve, and vein. The subject or the subject's in utero fetus may have any disorder involving a pathologic tissue membrane, including but not limited to ureteroceles, a congenital heart abnormality, an ovarian cyst, polycystic kidney disease, a posterior urethral valve, obstructive uropathy, acquired or congenital cystic kidney disease, calyceal diverticulum, acquired or congenital urethral stricture disease or ureteral stricture disease, congenital cystic adenomatoid malformation or other cystic lesions in a lung, need for a shunt in the brain or need for a bypass of cerebrospinal fluid or blood in the brain, a blockage in a Eustachian tube of the ear, congenital malformations of the esophagus, trachea, bowel or stomach such as pyloric stenosis, obstructed sinuses in the face or congenital or acquired obstruction of the uterus or vagina.

Thus, in one embodiment, the tissue may be a ureter and the subject or the subject's in utero fetus may have ureteroceles. In another embodiment, the tissue may be cardiac tissue and the subject or the subject's in utero fetus may have a congenital heart abnormality. In a further embodiment, the tissue may be an ovarian cyst. In yet another embodiment, the tissue may be a posterior urethral valve and the subject or the subject's in utero fetus may have obstructive uropathy. In a still further embodiment, the tissue may include a renal cyst and the subject may have acquired or congenital cystic kidney disease or calyceal diverticulum. In an additional embodiment, the tissue may include ureteral or urethral strictures and the subject may have acquired or congenital urethral stricture disease or ureteral stricture disease. In a further embodiment, the tissue may include lung and the subject may have congenital cystic adenomatoid malformation or other cystic lesions in a lung. In another embodiment, the tissue may include brain and the subject may need a shunt or a bypass of cerebrospinal fluid or blood. In still another embodiment, the tissue may include a tympanic membrane and the subject may have a blockage in the Eustachian tube of the ear. In a further embodiment, the tissue may include esophagus, trachea, bowel or stomach and the subject may have a congenital malformation or pyloric stenosis. In yet another embodiment, the tissue may include sinus and the subject may have an obstructed sinus. In an additional embodiment, the tissue may include uterus or vagina and the subject may have a congenital or acquired obstruction of the uterus or vagina.

As used herein, a "pathologic" tissue membrane means a tissue membrane structure that is causing an obstruction, blockage or mass or that is related to, involving or caused by an acquired or congenital disease or anomaly.

As used herein, "treat" or "treating" means accomplishing one or more of the following in an individual that is suffering from a pathologic tissue membrane: (a) reducing the severity of the pathologic tissue membrane, (b) inhibiting worsening of the pathologic tissue membrane; (c) limiting or preventing recurrence of the pathologic tissue membrane; (d) removal of all or a portion of the pathologic tissue membrane; (e) incising, cutting, puncturing, perforating or piercing all or a portion of the pathologic tissue membrane.

As used herein, an "effective amount" of the focused ultrasound refers to an amount of the ultrasound that is effective for treating a pathologic tissue membrane. The effective amount may vary from subject to subject, depending upon the age, the subject's size and health, the nature and extent of the condition being treated, recommendations of the treating physician, etc. For purposes of the present disclosure, generally a therapeutic amount of the focused ultrasound will be in the range of about 1 J to about 100,000 J, and may preferably be in the range of about 100 J to 3,000 J, which would correspond to about 10 seconds to 30 seconds of ultrasound therapy. The subject can be administered as many ultrasound treatments as are required to treat or limit the pathologic tissue membrane.

Figure 13:
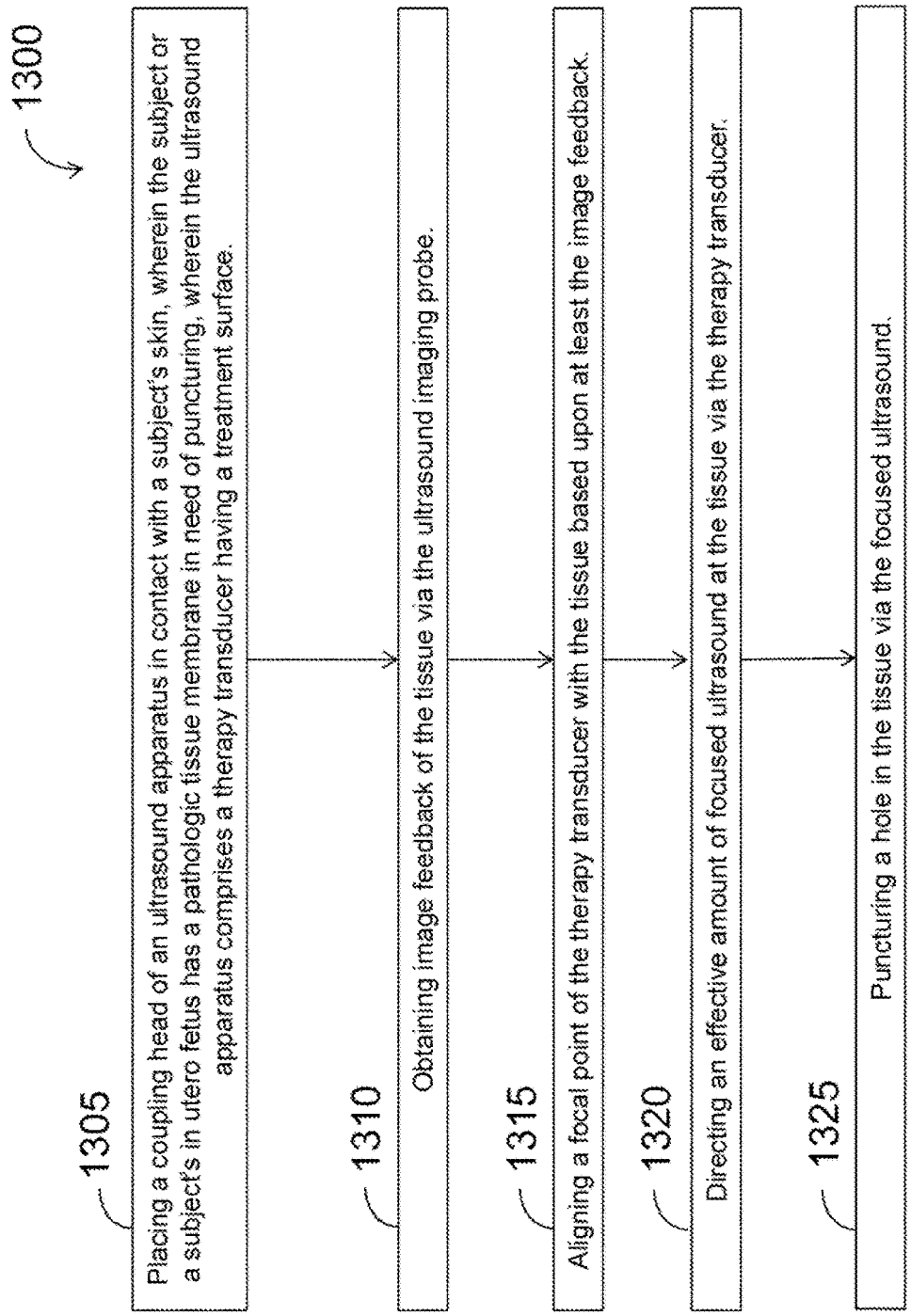
FIG. 13 is a flow chart of a method of treating a pathologic tissue membrane, according to one example embodiment.
Figure 14:
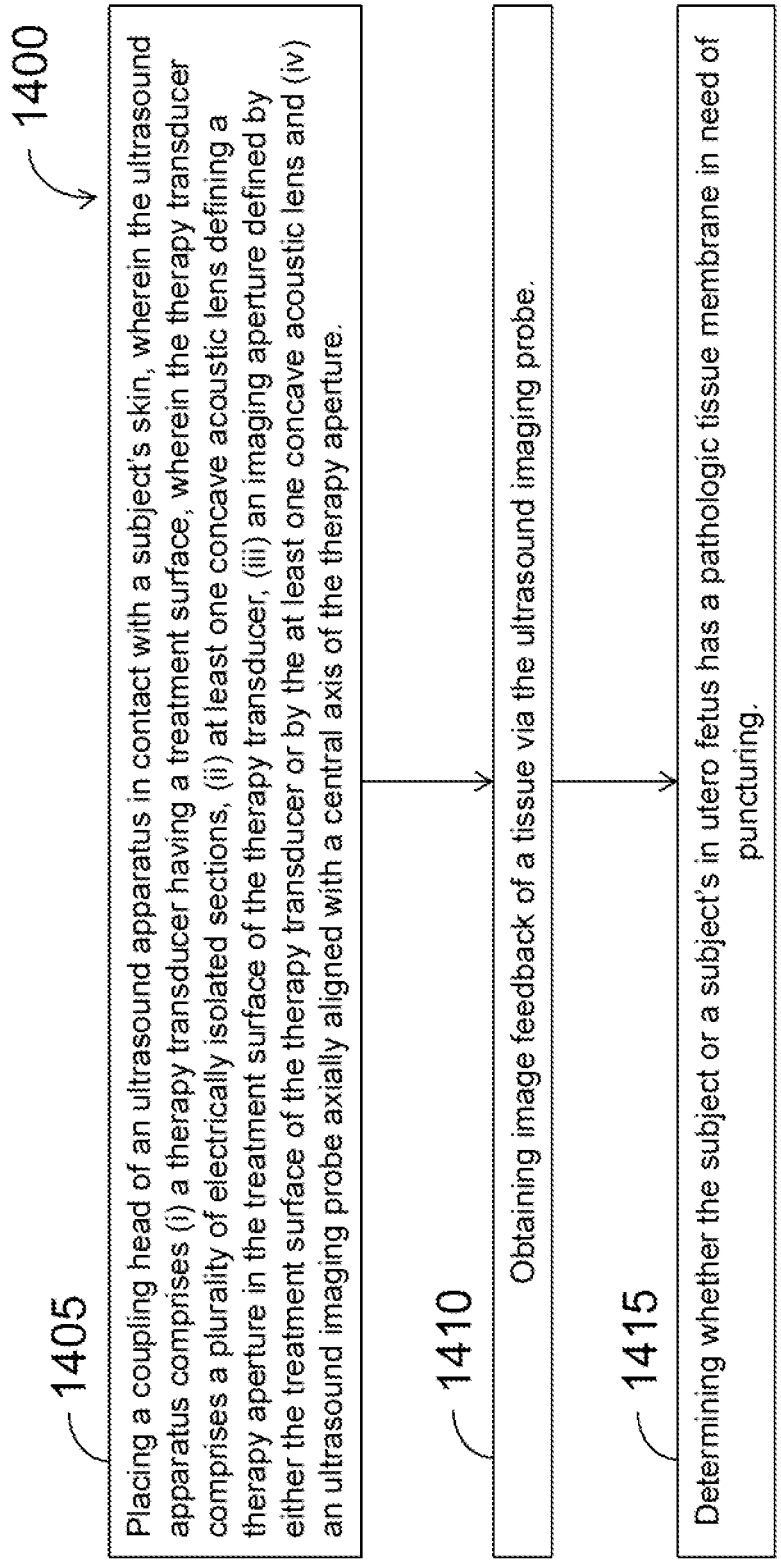
FIG. 14 is a flow chart of a method of diagnosing a pathologic tissue membrane, according to one example embodiment.

FIG. 13 is a flow chart of a method of treatment according to one example embodiment. Example methods, such as method 1300 of FIG. 13, may be carried out by an operator or a control system and/or by other components in communication with or disposed on the ultrasound apparatus. A control system may take the form of program instructions stored on a non-transitory computer readable medium and a processor that executes the instructions. However, a control system may take other forms including software, hardware, and/or firmware.

Example methods may be implemented as part of treating a pathologic tissue membrane. As shown by block 1305, method 1300 involves placing a coupling head of an ultrasound apparatus in contact with a subject's skin. The coupling head may be placed at any location on the body where a seal may be maintained between the coupling head and the subject's skin through which ultrasound may be directed. This location on the body may be external, for example on the subject's abdomen, back, limbs or skull, or internal via the rectum, vagina or esophagus, for example. The subject or a subject's in-utero fetus may have a pathologic tissue membrane in need of puncturing. The method may be performed using any of the embodiments of the ultrasound apparatus described above. Alternatively, the method for treatment may be carried out using a therapeutic focused ultrasound device having a single unitary concave transducer section defining a therapy aperture, where the concave transducer is configured to have a single electronic signal applied to it. Still further, the method for treatment may be carried out using an ultrasound device having a phased array in the form of a 2D grid that may permit modification of the location of the ultrasound focal point and the width of the focal point. At block 1310, the operator may obtain image feedback of the tissue via the ultrasound imaging probe. The image feedback may be displayed on, for example, a display device including a monitor, computer, laptop, LCD display, or any other device capable of displaying digital images or electronic files, among other possibilities. Then, at block 1315, the operator or the control system may align a focal point of the therapy transducer with the tissue based upon at least the image feedback. For example, an indicator showing the focal point of the therapy transducer may be overlaid on the ultrasound image on the display device. The operator may then manipulate the angle and/or placement of the therapy transducer relative to the subject in order to align the indicator with the desired region of the tissue. Alternatively, the operator may administer a short exposure of focused ultrasound to briefly generate cavitation bubbles that are visible via image feedback and confirm that the bubbles are located in the correct position without significantly affecting the tissue. Next, at block 1320, focused ultrasound is directed at the tissue via the therapy transducer. Finally, at block 1325, at least one hole or at least one linear incision is punctured in the tissue via the focused ultrasound. Puncture may be achieved through focused ultrasound-generated cavitation or boiling bubbles to controllably erode a hole or linear incision through the tissue.

In one embodiment, the punctured hole may have a diameter ranging from about 0.7 mm to about 3.4 mm. In various embodiments, the hole may be a single eroded hole. In other embodiments, there may be a series of smaller punctured holes that are achieved through slight realignment of the focal point of or high pressure zone created by the ultrasound apparatus, for example. In still further embodiments, the punctured hole may be an incised linear incision. The dimensions of the hole(s) or incision may be controlled by modifying ultrasound parameters described below to change the width of the ultrasound focal point.

In further embodiments, the directed focused ultrasound may be monitored via an imaging probe using one or more of a B-mode ultrasound imaging or Doppler ultrasound imaging. Then cavitation bubbles from the directed focused ultrasound may be detected in a flow channel through the eroded hole based upon at least the B-mode or Doppler ultrasound imaging. Once cavitation bubbles are detected, the directed focused ultrasound may be ceased.

In some embodiments, a fluid may be provided between the subject's skin and the coupling head. The directed focused ultrasound may then travel through at least the fluid and the patient's skin to the tissue, for example, the ureter. The fluid may take the form of ultrasound gel. The gel aids in coupling the ultrasound device to the subject's skin to allow the ultrasound an unbroken pathway to the intended focal point of the ultrasound apparatus.

In one embodiment, the focused ultrasound may be directed at the tissue for a duration of about 1 second to about 1 hour. For durations lasting 30 minutes or more, the subject may need to be anesthetized for pain management.

In another embodiment, using a control system coupled to an amplifier, the operator may set one or more of an ultrasound pulse duration, an ultrasound pulse repetition frequency, an ultrasound pulse time delay and an operating frequency of the therapy transducer. In an alternative embodiment, the foregoing parameters may be independently set for each of a plurality of electrically isolated sections of the therapy transducer. In one embodiment, altering the ultrasound pulse delay between the plurality of sections of the therapy transducer may permit the width of the ultrasound focal point or high pressure zone to be modified. For example, the signal for each electrically isolated section of the therapy transducer may be delayed more than the signal for the adjacent sections. Specifically, each signal for a given isolated section may be delayed by $t = m*n*T/N$, where "T" is the time period of one cycle of the ultrasound frequency. "N" is the total number of acoustic lens sectors, "n" is the specific order number of an isolated section in a given arrangement, and "m" is an integer. By setting the delays this way, the pulses may constructively interfere in a wider pressure region at the focal plane. If we choose "m" to be a larger number, the delays between the isolated sections may be larger, making the focal point wider. In another embodiment, increasing the ultrasound pulse duration may increase the diameter of the puncture or hole. In a further embodiment, the ultrasound pulse repetition frequency may be adjusted to assist in maintaining equal acoustic power distribution to each of the electrically isolated sections. In yet another embodiment, if all other parameters are maintained at the same level, then increasing the operating frequency of the transducer may more strongly focus the ultrasound to create a smaller hole. In various embodiments, the ultrasound pulse duration may range from about 1 μs to about 100 ms, the ultrasound pulse repetition frequency may range from about 1 Hz to about 10 kHz and the transducer operating frequency may range from about 0.2 MHz to about 10 MHz and preferably ranges from about 1 MHz to 3 MHz. In an alternative embodiment, the directed focused ultrasound may be continuous wave ultrasound.

In a further embodiment, the directed focused ultrasound may generate positive pressure that may range from about 30 MPa to about 120 MPa and negative pressure that may range from about 4 MPa to about 20 MPa. These pressure measurements are based on ultrasound measurements made in water, not through tissue. In addition, the positive and negative pressures may be larger depending on how the ultrasound is administered. For example, the pressure amplitudes required to achieve therapeutic effect depend upon the electrical parameters that may be set, as discussed above.

In still another embodiment, movement of the subject due to breathing or coughing, for example, and movement of the subject's in utero fetus may be detected via the ultrasound imaging probe or a sensor. In response to the detected movement, the directed focused ultrasound may be ceased temporarily until realignment is confirmed.

In still another aspect, the invention provides methods for diagnosing a pathologic tissue membrane, comprising:

placing a coupling head of an ultrasound apparatus in contact with a subject's skin, wherein the ultrasound apparatus comprises (a) a therapy transducer having a treatment surface, wherein the therapy transducer comprises a plurality of electrically isolated sections, (b) at least one concave acoustic lens defining a therapy aperture in the treatment surface of the therapy transducer, (c) an imaging aperture defined by either the treatment surface of the therapy transducer or by the at least one concave acoustic lens and (d) an ultrasound imaging probe axially aligned with a central axis of the therapy aperture;

obtaining image feedback of a tissue via the ultrasound imaging probe; and determining whether the subject or a subject's in utero fetus has a pathologic tissue membrane in need of puncturing.

As disclosed herein, the inventors have discovered that the methods of this aspect of the invention can be used, for example, to determine whether the subject or a subject's in utero fetus has a pathologic tissue membrane in need of puncturing. B-Mode ultrasound imaging or Doppler imaging may be used via an imaging probe to obtain images of a tissue suspected of contributing to symptoms exhibited by the subject The methods of the invention can be used to diagnose any suitable subject, such as a human subject with a pathologic tissue membrane that may benefit from controllably eroding a hole through the tissue with the defect. In various non-limiting embodiments, the pathologic tissue membrane may be in a tissue, including but not limited to ureter, urethra, cardiac tissue, bladder, prostate, cyst, kidney, liver, nerve, artery, sail, sheath, penis, uterus, vagina, lung, brain, tympanic membrane, valve, and vein. The subject or the subject's in utero fetus may have any disorder involving a pathologic tissue membrane, including but not limited to ureteroceles, a congenital heart abnormality, an ovarian cyst, polycystic kidney disease, a posterior urethral valve, obstructive uropathy, acquired or congenital cystic kidney disease, calyceal diverticulum, acquired or congenital urethral stricture disease or ureteral stricture disease, congenital cystic adenomatoid malformation or other cystic lesions in a lung, need for a shunt in the brain or need for a bypass of cerebrospinal fluid or blood in the brain, a blockage in a Eustachian tube of the ear, congenital malformations of the esophagus, trachea, bowel or stomach such as pyloric stenosis, obstructed sinuses in the face or congenital or acquired obstruction of the uterus or vagina.

Thus, in one embodiment, the tissue may be a ureter and the subject or the subject's in utero fetus may have ureteroceles. In another embodiment, the tissue may be cardiac tissue and the subject or the subject's in utero fetus may have a congenital heart abnormality. In a further embodiment, the tissue may be an ovarian cyst. In yet another embodiment, the tissue may be a posterior urethral valve and the subject or the subject's in utero fetus may have obstructive uropathy. In a still further embodiment, the tissue may include a renal cyst and the subject may have acquired or congenital cystic kidney disease or calyceal diverticulum. In an additional embodiment, the tissue may include ureteral or urethral strictures and the subject may have acquired or congenital urethral stricture disease or ureteral stricture disease. In a further embodiment, the tissue may include lung and the subject may have congenital cystic adenomatoid malformation or other cystic lesions in a lung. In another embodiment, the tissue may include brain and the subject may need a shunt or a bypass of cerebrospinal fluid or blood. In still another embodiment, the tissue may include a tympanic membrane and the subject may have a blockage in the Eustachian tube of the ear. In a further embodiment, the tissue may include esophagus, trachea, bowel or stomach and the subject may have a congenital malformation or pyloric stenosis. In yet another embodiment, the tissue may include sinus and the subject may have an obstructed sinus. In an additional embodiment, the tissue may include uterus or vagina and the subject may have a congenital or acquired obstruction of the uterus or vagina.

Example methods may be implemented as part of diagnosing a pathologic tissue membrane. As shown by block 1405, method 1400 involves placing a coupling head of an ultrasound apparatus in contact with a subject's skin. In one embodiment, the ultrasound apparatus may include (a) a therapy transducer having a treatment surface, wherein the therapy transducer comprises a plurality of electrically isolated sections, (b) at least one concave acoustic lens defining a therapy aperture in the treatment surface of the therapy transducer, (c) an imaging aperture defined by either the treatment surface of the therapy transducer or by the at least one concave acoustic lens and (d) an ultrasound imaging probe axially aligned with a central axis of the therapy aperture. The coupling head may be placed at any location on the body where a seal may be maintained between the coupling head and the subject's skin through which ultrasound may be directed for diagnosis. This location on the body may be external, for example on the subject's abdomen, back, limbs or skull, or internal via the rectum, vagina or esophagus for example. The method may be performed using any of the embodiments of the ultrasound apparatus described above. At block 1410, the operator may obtain image feedback of a tissue via the ultrasound imaging probe. The image feedback may be displayed on, for example, a monitor, computer, laptop. LCD display, or any other device capable of displaying digital images or electronic files, among other possibilities. Then, at block 1415, the operator or the control system may determine whether the subject or a subject's in utero fetus has a pathologic tissue membrane in need of puncturing.

The above detailed description describes various features and functions of the disclosed apparatus and methods with reference to the accompanying figures. While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

Example 1

Methods:

Fresh bovine bladder was used to create two models for the ureterocele wall. The first was a bleb model created by injection of 1-2 mL dyed normal saline into the submucosal layer. The second was a denuded mucosal membrane separated from the muscular layer. The tissue was positioned in a degassed water bath and the target layer was aligned with the focus of a 1 MHz ultrasound transducer. Pulsed focused ultrasound was administered to create a visible hole in the wall. The pulse amplitudes employed were similar to those applied for extracorporeal shockwave lithotripsy, with peak positive pressure p+=100-120 MPa and peak negative pressure of 17-20 MPa. Pulse duration and pulse rate were varied between different exposures. Time to puncture and puncture size were recorded. The use of ultrasound imaging as a method of targeting and treatment feedback was also explored.

Figure 8:
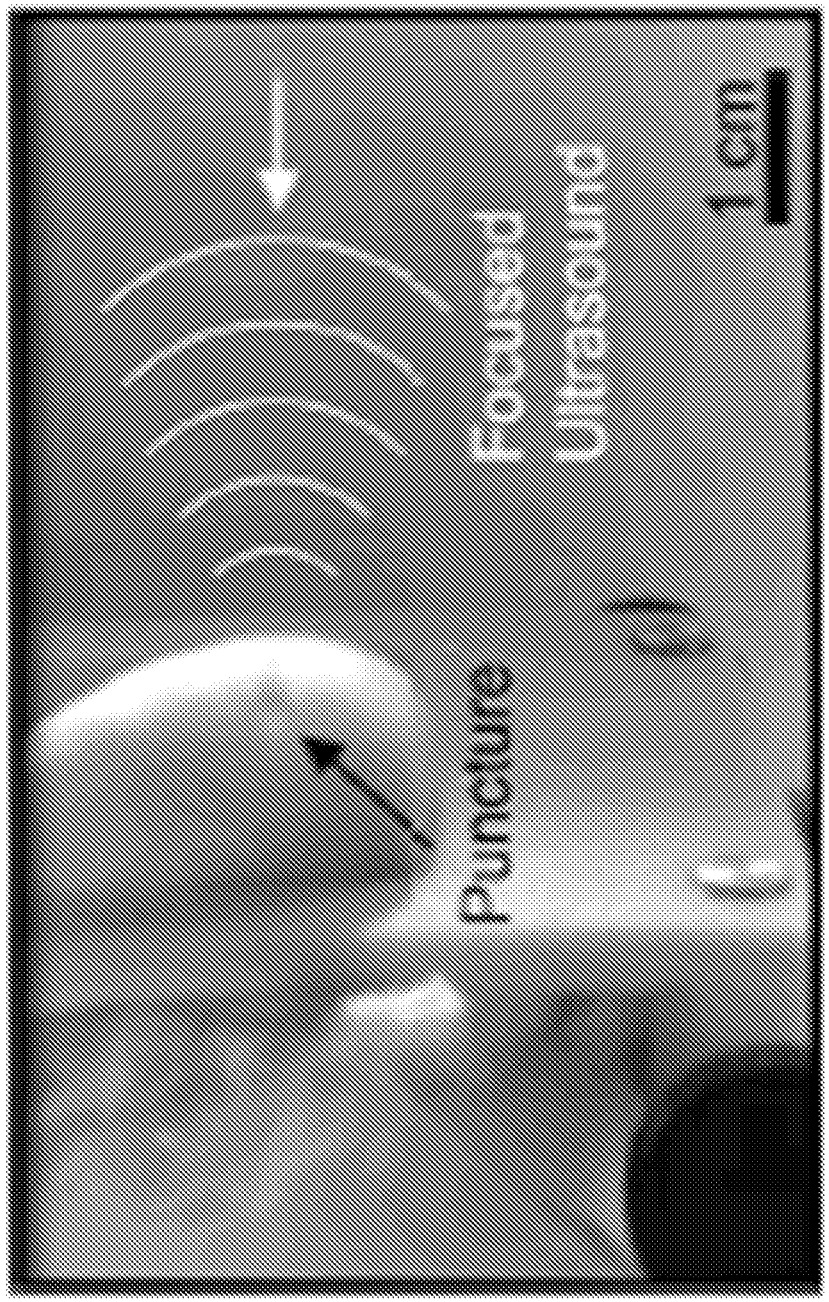
FIG. 8 shows a puncture created in a bladder bleb after 180 seconds exposure of high-intensity ultrasound (indicated by white radiating lines) focused onto the bleb wall in accordance with Example 1 below.

Results:

Focused ultrasound produced erosion of the wall and puncture (FIG. 8) in times between 50-300 seconds, depending on ultrasonic parameters, focal alignment, and wall thickness. For example, FIG. 8 shows a puncture created in a bladder bleb after 180 seconds exposure of high-intensity ultrasound (indicated by white radiating lines) focused onto the bleb wall. Dye was visible flowing from the punctures post-treatment, indicating the existence of a patent communication through the wall. The resulting hole diameters were between 0.5 to 3 mm and were highly consistent for a given acoustic exposure (n=4-6). No damage to the wall was apparent outside of the focal zone. Cavitation was visualized on B-mode ultrasound imaging within the focal zone as a hyperechoic region, providing precise targeting for the extent of erosion.

Conclusion:

Focused ultrasound-induced cavitation can generate precise punctures in the inner bladder wall similar to those created endoscopically for treatment of ureteroceles. Results suggest B-Mode ultrasound imaging can be used for guidance the procedure.

Example 2

In the present example, the feasibility of using histotripsy to generate a mechanical puncture under ultrasound image guidance was evaluate using a tissue model for the ureterocele wall.

Materials and Methods:

A model of the ureterocele wall was developed using freshly excised bovine bladder tissue. The bladder was harvested and maintained in degassed phosphate-buffered saline until use (<12 hours from excision). The bladder was sectioned into 5×5 cm segments. The mucosal and submucosal layers were denuded from the underlying muscle and adventitia to create a membrane 0.5-1 mm in thickness. The mucosal membrane was placed over a circular opening of a polypropylene chamber containing dyed saline. The membrane was fixed with a band around the container such that the membrane sealed the fluid in the chamber without applying tension to the membrane, aside from that caused by the sample's own weight. This model provided an end point for determination of puncture when dyed saline could be observed flowing through the puncture hole in the membrane.

A custom ultrasound therapy system constructed in the laboratory was used to deliver focused ultrasound energy to the samples. The therapy transducer was a 1 MHz seven-element array with 14.7-cm diameter. Each element of the transducer was focused through a plastic lens, with all lenses focused at the radius of curvature of 14 cm. The transducer was electrically driven by a radiofrequency class D amplifier modified to output high amplitude pulse durations up to 10 ms. The amplifier output was controlled by an electronic timing board that specified the ultrasound pulse duration ("PD"), pulse repetition rate ("PRF"), and transducer operating frequency.

The three-dimensional pressure output of the transducer was obtained under free field conditions in a degassed water bath by acoustic holography with a capsule hydrophone (HGL-0085. Onda Corporation, Sunnyvale, Calif.) recorded at low pressure amplitudes and nonlinear acoustic simulation. The focal pressures were confirmed by measurements with a fiberoptic probe hydrophone (FOPH2000. RP Acoustics. Stuttgart, Germany). The linear −6 dB focal pressure beam width was 2.0 mm transverse to the acoustic axis by 13.6 mm along the acoustic axis. The focal peak positive pressure of the ultrasound pulses applied in this experiment was 100-120 MPa, and the peak negative pressure applied was 17-20 MPa. Pulses between 1-5000 cycles duration were used in the experiments, with the pulse rate selected in each case to fix the duty cycle at 0.5% to 0.6%. Correspondingly, the time-averaged spatial peak intensity of the exposure was between 145-190 W/cm$^2$.

A research ultrasound imaging engine (V-1. Verasonics Inc., Redmond. Wash.) with a linear array probe (L7-4, Philips Healthcare, Andover, Mass.) operated at 5 MHz was used to visualize the treatment area before, during, and after exposure in a subset of the experiments. The imaging was triggered by the therapy system such that the images were synchronized to avoid acoustic and electrical interference from the therapy ultrasound pulses. Because of the low duty factor of the therapy output (≤1%), the frame rate of the ultrasound imager could be maintained at ≥10 frames per second during treatment.

Figure 9:
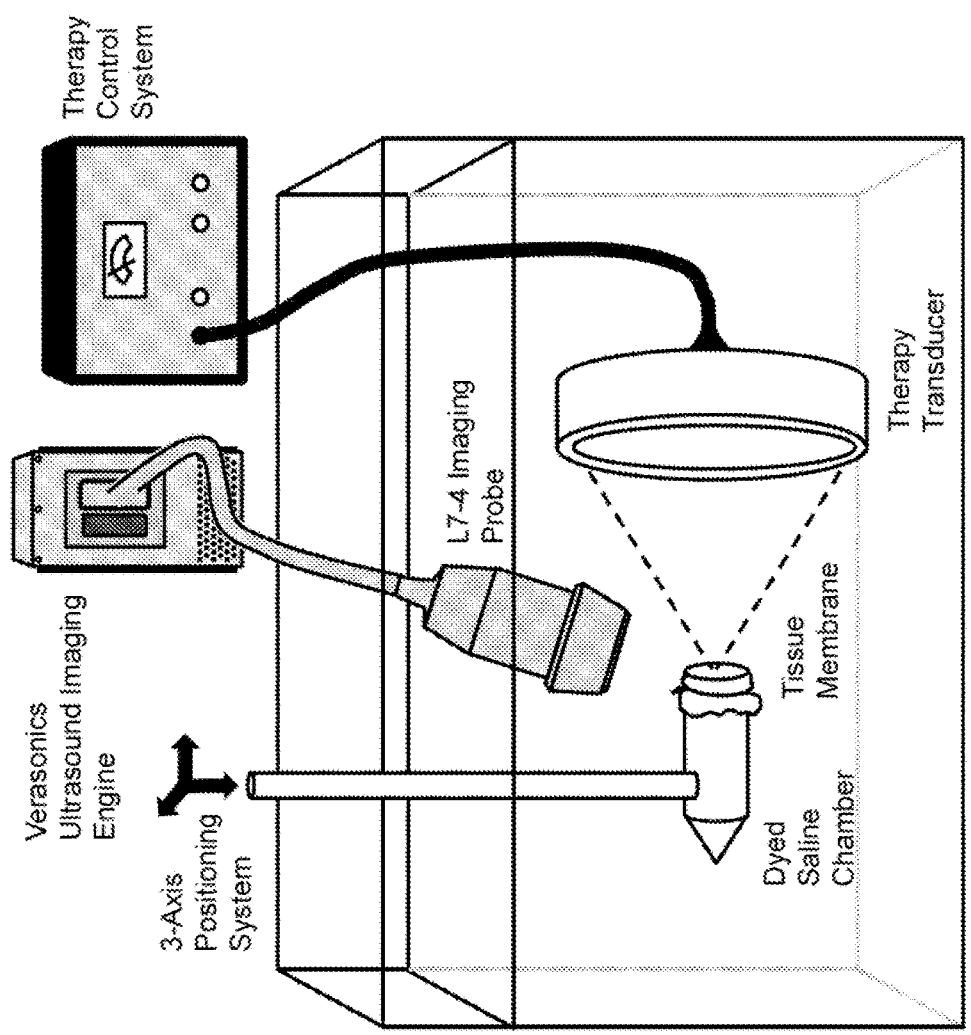
FIG. 9 shows the experimental alignment of a sample with therapy and imaging transducers during exposure in accordance with Example 2 below. The sample is shown sealed over a chamber of dyed saline and attached to a three-axis motor positioner to align it with the therapy transducer focus. An imaging probe was positioned at an oblique angle in the focal plane to observe the cavitation activity of the sample pre- and post-puncture.

The sample, along with the therapy and imaging transducers, was positioned in a degassed, filtered water bath (FIG. 9). For example, FIG. 9 shows the experimental alignment of a sample with therapy and imaging transducers during exposure. The sample is shown sealed over a chamber of dyed saline and attached to a three-axis motor positioner (Velmex Inc., Bloomfield, N.Y.) to align it with the therapy transducer focus. An imaging probe was positioned at an oblique angle in the focal plane to observe the cavitation activity of the sample pre- and post-puncture. An alignment laser was used to identify the position of the focus in the water. Next, the membrane was translated by the three-axis motorized positioner aligning the tissue with the therapy transducer focus. A short, 1-second exposure was then used to confirm alignment by visualization of cavitation on the membrane. The imaging probe was aligned off-axis in the water bath in the plane of the therapy focus to observe the treatment region. A digital camera (S8000, Nikon USA, Melville, N.Y.) was used to record a video of each exposure.

The membrane was exposed under a set of ultrasound therapy pulse parameters until a visual puncture through the membrane was observed. In some cases, punctures were falsely identified, and no dye was visualized flowing through the membrane when the therapy was turned off. In these cases, the membrane was further treated until a positive result was achieved for up to 300 seconds total treatment time. After treatments, the punctures were photographed and measured while still attached to the container outside of the water bath.

Figures 10A, 10B:
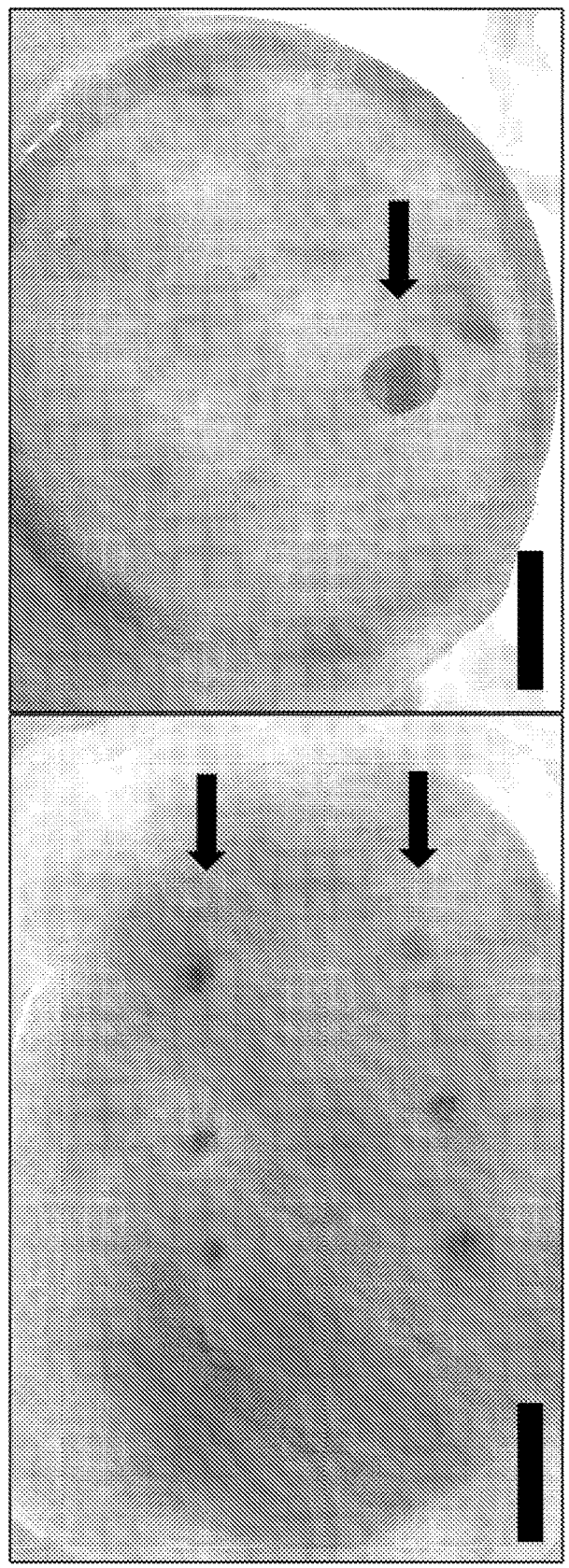
FIG. 10A shows six punctures made in the sample bladder wall membrane by exposures with a short pulse duration (2 µs) of an ultrasound in accordance with Example 2 below. The scale bar is 5 mm long.
FIG. 10B shows a larger puncture generated by a sequential exposure of 1 µs pulses followed by 5000 µs pulses in accordance with Example 2 below. The scale bar is 5 mm long.
Figure 11:
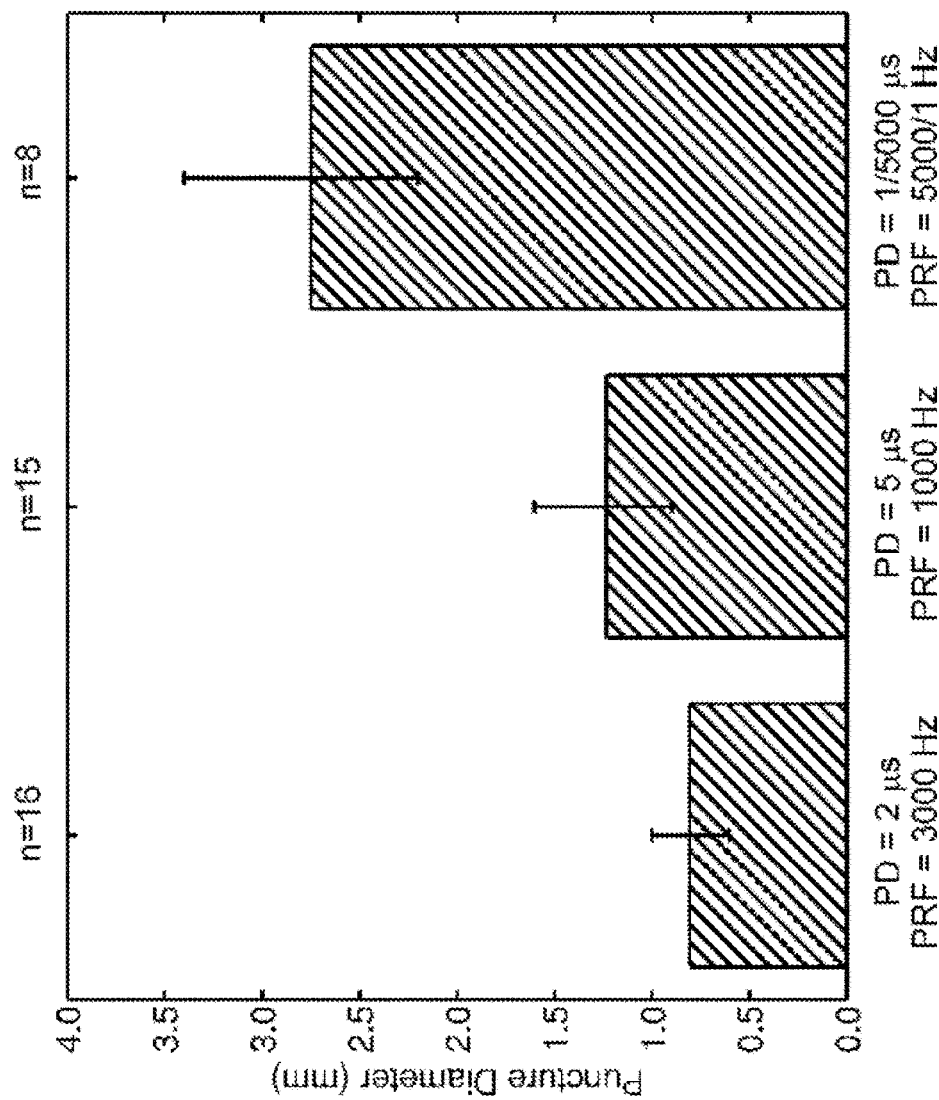
FIG. 11 shows a graph illustration mean puncture diameter versus duration of pulses in the exposure in accordance with Example 2 below. Error bars indicate the range of puncture sizes observed. PD=pulse duration and PRF=pulse repetition frequency.

Results:

A localized cloud of cavitation bubbles was observed during ultrasound exposure at the focus of the therapy transducer on the sample wall. Puncture was achieved in the samples using three different acoustic parameter sets. Blue dye was visible leaking through the membrane once the treatment was terminated, indicating a communication was formed. Puncture diameter was consistent for a given set of exposure parameters, even with different sample thicknesses (n=8-16 punctures) (FIGS. 10A-B, 11). For example, FIG. 10A shows six punctures made in the sample bladder wall membrane by exposures with a short pulse duration (2 μs) of an ultrasound (the scale bar is 5 mm long), whereas FIG. 10B shows a larger puncture generated by a sequential exposure of 1 μs pulses followed by 5000 its pulses (the scale bar is 5 mm long). FIG. 11, in turn, shows a graph illustration mean puncture diameter versus duration of pulses in the exposure, where error bars indicate the range of puncture sizes observed (PD=pulse duration and PRF=pulse repetition frequency). Puncture diameter was smallest (0.8±0.1 mm, mean-standard deviation) with a short PD of 2 μs delivered at PRF=3000 Hz. Punctures were significantly larger (1.2±0.2 mm. P<0.001) with PD=5 μs delivered at PRF=1000 Hz. The exposure time necessary to achieve a puncture varied with the thickness of the membrane, but was not significantly different between these two parameter sets (151±63 seconds, PD=2 μs vs 131±64 s, PD=5 μs).

Exposures using a much longer PD applied at a low PRF did not form a complete puncture within the 300 second time window. Once a small puncture was formed, however, such pulses effectively expanded the perforation diameter. This outcome was demonstrated by first using a short PD (1 μs) at high PRF (5000 Hz), then delivering to the same location pulses with PD=5000 its at PRF=1 Hz, which expanded the puncture to a final dimension of 2.8±0.4 mm.

Figure 12:
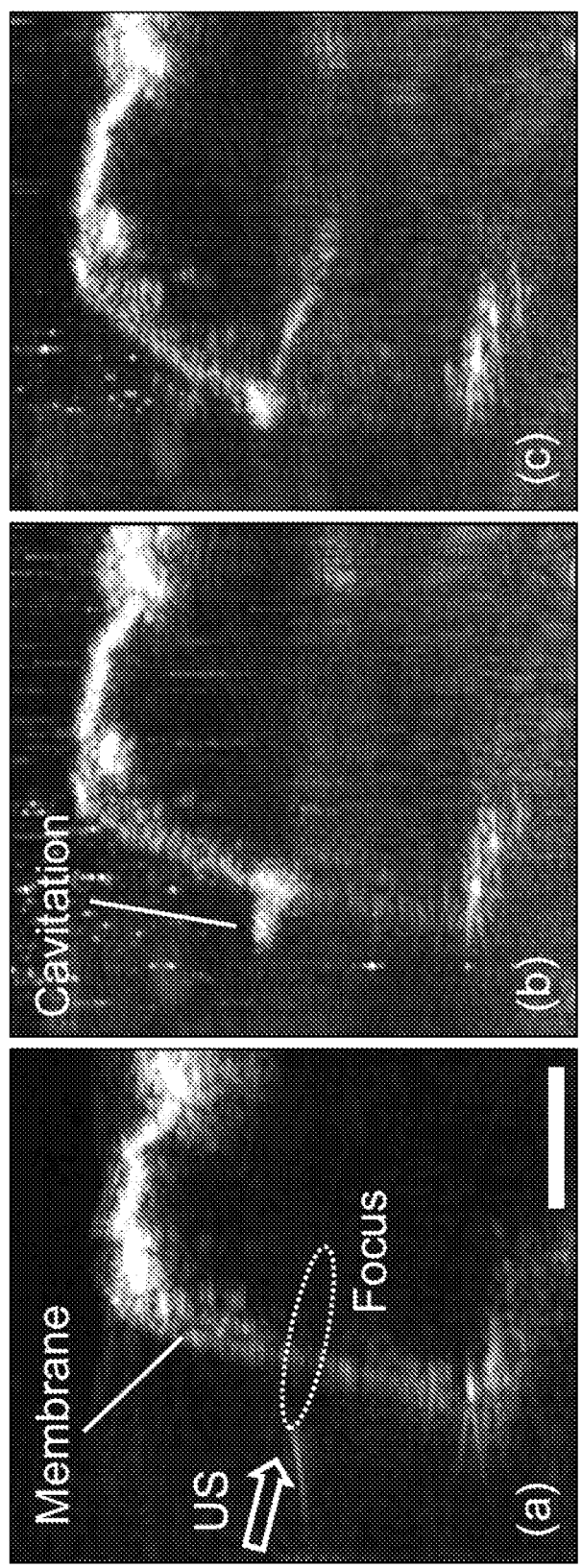
FIG. 12A shows the therapy ultrasound orientation and focusing in accordance with Example 2 below. The visualization of bladder mucosa by B-mode ultrasound image guidance is shown before treatment. The scale bar is 1 cm.
FIG. 12B shows the visualization of bladder mucosa by B-mode ultrasound image guidance during exposure pre-puncture in accordance with Example 2 below. Cavitation is shown to be localized to the external membrane surface before puncture.
FIG. 12C shows the visualization of bladder mucosa by B-mode ultrasound image guidance during exposure post-puncture in accordance with Example 2 below. Once a channel is created, bubbles can be seen flowing through the membrane.

Ultrasound B-mode images indicated the presence of cavitation as an echogenic region at the focal point (FIGS. 12A-C). For example, FIG. 12A shows the therapy ultrasound orientation and focusing, and the visualization of bladder mucosa by B-mode ultrasound image guidance is shown before treatment (the scale bar is 1 cm). Before puncture, cavitation was limited to the proximal membrane surface (transducer side). Then, cavitation is shown to be localized to the external membrane surface before puncture. Specifically, FIG. 12B shows the visualization of bladder mucosa by B-mode ultrasound image guidance during exposure pre-puncture. Finally, cavitation was visualized penetrating into, and eventually through, the membrane, forming a narrow jet in the fluid space distal to the surface. This phenomenon is shown in FIG. 12C, which displays the visualization of bladder mucosa by B-mode ultrasound image guidance during exposure post-puncture. The puncture was not visible after treatment as a hypoechoic region in the membrane, as is apparent on bulk tissues treated by histotripsy. However, once a channel was created, bubbles could be seen flowing through the membrane, as shown in FIG. 12C.

Discussion:

Current methods of ureterocele treatment include minimally invasive endoscopic puncture and open surgery. This study identified a potential noninvasive method using focused ultrasound to create a puncture in ureteroceles under ultrasound image guidance. Ideally, the treatment would be delivered without general anesthesia as an office-based procedure using a hand-held transducer the size of a diagnostic ultrasound imager. The current experimental exposure time of ~2 to 3 minutes, however, may be longer than desirable to avoid anesthesia. The time to puncture varied significantly between samples, possibly because of variation in properties of the sample that were not carefully controlled in this study, such as membrane thickness, tension, and curvature. Puncture may be achievable over a shorter time using acoustic parameters outside of the range tested. The level of pain experienced during such a procedure is not known and will have to be evaluated carefully to determine an appropriate level of sedation.

The treatment times found indicate that the bladder wall needs a significantly greater acoustic dose to disintegrate than that needed to ablate soft, parenchymal tissues with histotripsy. It is not clear, however, how well the model used mimics the true mechanical properties of the ureterocele wall. Despite the tissue resilience, perforations were reliably achieved with a controllable size and location. The flexibility to alter puncture size may allow the clinician to optimize the technology for individual treatments.

There are currently several techniques used for decompression without an accepted standard. Decompression has been achieved with a single puncture as small as 3 F. or a transverse incision of 2 to 3 mm. A retrospective analysis found no indication of correlation between puncture techniques with outcomes. Recent studies, however, suggest alternate puncture patterns could reduce the risk of vesicoureteral reflux over a simple single incision. Future refinement of both the model and the therapy system will aid in better assessing the clinical parameters.

The results also suggest that ultrasound imaging may provide feedback to the operator for precise position of treatment and detection of the puncture. It was possible to detect a perforation when therapy was being delivered with cavitation observed on both sides of the ureterocele. There is a tendency for formation of a cavitation cloud at the fluid-tissue interface that possibly arises from bubbles being preferentially pushed into the membrane by acoustic radiation force. On puncture, this force would cause bubbles to flow through the hole, as observed on B-mode images. The hole was not visible directly under B-mode ultrasonography post-treatment, however. Color Doppler Ultrasound may complement B-mode imaging feedback in providing information on the flow channel created after therapy and help determine a more precise end point. In addition to neonatal surgery, another application may be the management of ureteroceles in utero.

Conclusions:

Pulsed focused ultrasound can create a mechanical perforation in denuded bladder mucosa, a tissue model for the ureterocele wall. The puncture diameter was repeatable and could be controlled by ultrasound exposure parameters. Ultrasound imaging allowed for real-time targeting and visualization to confirm puncture. These results indicate that histotripsy as a noninvasive method of ureterocele puncture is feasible.

The invention claimed is:

1. An ultrasound apparatus, comprising:
a therapy transducer having a treatment surface, wherein the therapy transducer comprises a plurality of electrically isolated sections, each comprising a flat piezoelectric material;
at least one concave acoustic lens defining a therapy aperture in the treatment surface of the therapy transducer;
an imaging aperture defined by either the treatment surface of the therapy transducer or by the at least one concave acoustic lens; and
an ultrasound imaging probe axially aligned with a central axis of the therapy aperture;
wherein the at least one concave acoustic lens is a single concave acoustic lens that comprises a plurality of sectors each having a radius of curvature, and wherein each of the plurality of electrically isolated sections of the therapy transducer is coupled to one of the plurality of sectors of the single acoustic lens; and/or
wherein the at least one concave acoustic lens is a plurality of concave acoustic lenses each having a radius of curvature, wherein each of the plurality of electrically isolated sections of the therapy transducer is coupled to one of the plurality of acoustic lenses;
wherein each said radius of curvature is defined by a concave elliptical profile such that the major axis is aligned in the direction towards the focal point of the transducer.

2. The ultrasound apparatus of claim 1, wherein the at least one concave acoustic lens is a single concave acoustic lens, wherein the single acoustic lens defines the imaging aperture, wherein the single acoustic lens comprises a plurality of sectors each having a radius of curvature, and wherein each of the plurality of electrically isolated sections of the therapy transducer is coupled to one of the plurality of sectors of the single acoustic lens.

3. The ultrasound apparatus of claim 2, wherein the plurality of sectors of the acoustic lens is between 4 sectors to 100 sectors.

4. The ultrasound apparatus of claim 2, wherein the radius of curvature of each of the plurality of sectors of the acoustic lens is smaller than a radius of curvature of the acoustic lens.

5. The ultrasound apparatus of claim 2, wherein the radius of curvature of each of the plurality of sectors of the acoustic lens is the same.

6. The ultrasound apparatus of claim 2, wherein the radius of curvature of each of the plurality of electrically isolated sections of the therapy transducer is smaller than a radius of curvature of the single acoustic lens.

7. The ultrasound apparatus of claim 2, wherein each of the plurality of sectors is configured to direct ultrasound to a focal point, and wherein the focal point lies on the central axis of the therapy aperture and ranges from about 1 cm to about 18 cm from a center of the therapy aperture.

8. The ultrasound apparatus of claim 1, wherein the at least one concave acoustic lens is a plurality of concave acoustic lenses, wherein each of the plurality of electrically isolated sections of the therapy transducer is coupled to one of the plurality of acoustic lenses.

9. The ultrasound apparatus of claim 8, wherein the plurality of concave acoustic lenses is between 4 acoustic lenses to 100 acoustic lenses.

10. The ultrasound apparatus of claim 1, wherein the plurality of electrically isolated sections of the therapy transducer each have a radius of curvature and together define a single acoustic lens.

11. The ultrasound apparatus of claim 1, wherein the plurality of electrically isolated sections of the therapy transducer comprises between 4 sections and 1000 sections.

12. The ultrasound apparatus of claim 1, further comprising:
a coupling head coupled to and extending from the treatment surface of the therapy transducer.

13. The ultrasound apparatus of claim 12, wherein the coupling head is angled inward toward the central axis of the therapy aperture.

14. The ultrasound apparatus of claim 12, wherein the coupling head circumscribes the at least one acoustic lens.

15. The ultrasound apparatus of claim 12, wherein the coupling head comprises a membrane, and wherein a fluid is enclosed between the at least one acoustic lens and the membrane of the coupling head.

16. The ultrasound apparatus of claim 12, wherein the coupling head comprises a solid planar disc.

17. The ultrasound apparatus of claim 1, further comprising a housing at least partially surrounding the plurality of electrically isolated sections of the therapy transducer and the imaging probe.

18. The ultrasound apparatus of claim 1, further comprising:
an amplifier coupled to the therapy transducer.

19. The ultrasound apparatus of claim 18, further comprising:
a control system configured to control the amplifier.

* * * * *